United States Patent [19]
Bloom et al.

[11] Patent Number: 5,854,055
[45] Date of Patent: *Dec. 29, 1998

[54] RECOMBINANT MYCOBACTERIA

[75] Inventors: Barry R. Bloom, Hastings on Hudson; William R. Jacobs, Jr., Bronx, both of N.Y.; Ronald W. Davis, Palo Alto, Calif.; Richard A. Young, Winchester, Mass.; Robert N. Husson, Takoma Park, Md.

[73] Assignee: Albert Einstein College of Medicine of Yeshiva University, a Division of Yeshiva University, Bronx, N.Y.

[*] Notice: The term of this patent shall not extend beyond the expiration date of Pat. No. 5,504,005.

[21] Appl. No.: 463,942

[22] Filed: Jun. 5, 1995

Related U.S. Application Data

[63] Continuation of Ser. No. 361,944, Jun. 5, 1989, Pat. No. 5,504,005, which is a continuation-in-part of Ser. No. 223,089, Jul. 22, 1988, abandoned, and Ser. No. 216,390, Jul. 7, 1988, abandoned, said Ser. No. 361,944, Ser. No. 223,089, and Ser. No. 216,390, which is a continuation-in-part of Ser. No. 163,546, Mar. 3, 1988, abandoned, which is a continuation-in-part of Ser. No. 020,451, Mar. 2, 1987, abandoned.

[51] Int. Cl.$^6$ .......................... C12N 15/64; C12N 15/66; C12N 15/74
[52] U.S. Cl. .................... 435/253.1; 435/69.1; 435/69.8; 435/71.1; 435/172.1; 435/172.3; 435/252.3
[58] Field of Search .................. 435/69.1, 71.1, 435/172.1, 172.3, 252.3, 253.1, 69.8; 935/52, 72

Primary Examiner—David Guzo
Assistant Examiner—Sean MGarry
Attorney, Agent, or Firm—Amster, Rothstein & Ebenstein

[57] ABSTRACT

Recombinant mycobacterial vaccine vehicles capable of expressing DNA of interest which encodes at least one protein antigen for at least one pathogen against which an immune response is desired and which can be incorporated into the mycobacteria or stably integrated into the mycobacterial genome. The vaccine vehicles are useful for administration to mammalian hosts for purposes of immunization. A recombinant vector which replicates in *E. coli* but not in mycobacteria is also disclosed. The recombinant vector includes 1) a mycobacterial gene or portions thereof, necessary for recombination with homologous sequences in the genome of mycobacteria transformed with the recombinant plasmid; 2) all or a portion of a gene which encodes a polypeptide or protein whose expression is desired in mycobacteria transformed with the recombinant plasmid; 3) DNA sequences necessary for replication and selection in *E. coli*; and 4) DNA sequences necessary for selection in mycobacteria (e.g., drug resistance). The present invention also relates to two types of recombinant vectors useful in introducing DNA of interest into mycobacteria, where it is expressed. One type of vector is a recombinant plasmid capable of replicating as a plasmid in *E. coli* and of lysogenizing a mycobacterial host. The other type of vector is a recombinant plasmid which can be introduced into mycobacteria, where it is stably maintained extrachromosomally.

19 Claims, 17 Drawing Sheets

Library of 11.2 kb pIJ666 :: pAL5000 Recombinant Plasmids

Expression of the M. leprae 65 kDa Antigen in BCG

FIG. 17 pYUB39 = pYUB12 :: M. leprae 65 kDa gene

RECOMBINANT MYCOBACTERIA

RELATED APPLICATIONS

This application is a continuation of application Ser. No. 07/361,944, now U.S. Pat. No. 5,504,005, filed Jun. 5, 1989, entitled "Recombinant Mycobacterial Vaccine", which is a continuation-in-part of application Ser. No. 07/223,089, now abandoned, filed Jul. 22, 1988, entitled "Stable Expression of Cloned Genes in Mycobacteria Using Phage and Plasmid Vectors" and of application Ser. No. 07/216,390, now abandoned, filed Jul. 7, 1988, entitled "Recombinant Mycobacteria Having DNA of Interest Stably Integrated Into Genomic DNA, which are contination-in-part applications of application Ser. No. 07/163,546, now abandoned, filed Mar. 3, 1988, entitled "Recombinant Mycobacterial Vaccine", which is a continuation-in-part of application Ser. No. 07/020,451, now abandoned, filed Mar. 2, 1987, entitled "Recombinant Mycobacterial Vaccine." The teachings of these four related applications are incorporated herein by reference.

FUNDING

Work described herein was supported by funding from the World Health Organization, Albert Einstein College of Medicine of Yeshiva University, The Whitehead Institute for Biomedical Research, the National Institutes of Health, and the Rockefellar Foundation.

BACKGROUND

Immunization

Immunity to a foreign antigen (e.g., a pathogen or toxin) can be provided by passive transfer or active induction. In the former case, antibodies against the foreign protein pathogen are injected into an individual, with the result that short-term protection is provided. In the latter case, injection of a harmless (innocuous) form of the pathogen, a component of the pathogen, or a modified form of the toxin (i.e., a toxoid) stimulates the individual's immune system, conferring long-term protection.

Active immunity can be induced, provided an individual's immune system is competent, by using an appropriate antigen to stimulate the immune system. For example, immunization (vaccination) with an innocuous or attenuated form of the pathogen in this manner results in an immediate immune response, as well as immunological "memory", thus conferring long-term protection as well. In general, vaccines include inactivated, nonpathogenic or attenuated forms of a pathogen or infectious agent, which include antigenic determinants of the pathogen and thus elicit an immune response. Similarly, toxins, which are antigenic substances produced by microorganisms, plants and animals, can be converted to toxoids; that is, they can be modified to destroy their toxic properties but retain their antigenicity and, as a result, their ability to stimulate production of antitoxin antibodies and produce active immunity. Such toxoids can be used for vaccines against the toxin.

In both cases—that involving stimulation of an immune response by administration of an altered form of an infectious pathogen and that involving administration of a toxoid—presently-available procedures are generally effective, but side effects and deaths resulting from the vaccination are known to occur.

Safer vaccines are now being developed through application of better knowledge of the antigenic determinants of a pathogen and of genetic engineering/recombinant DNA techniques. For example, it is possible to make a polypeptide (e.g. by chemical synthesis or expression of DNA encoding the polypeptide of interest) which is a component (e.g., an antigenic determinant) of a protein antigen known to elicit an immune response. Administration of the polypeptide to a host is followed by an immune response by the host to the antigenic determinant. Use of such a polypeptide is not accompanied by the risk of infection which accompanies use of live or attenuated vaccines.

Immunization (administration of a vaccine) is a common and widespread procedure and the vaccine used can be essentially "any preparation intended for active immunological prophylaxis", including preparations of killed microbes of virulent strains, living microbes of attenuated strains, and microbial, fungal, plant, protozoal or metazoan derivatives or products. *Stedman's Illustrated Medical Dictionary* (24th edition), Williams & Wilkins, Baltimore, p. 1526 (1982). In many cases, vaccines must be administered more than once in order to induce effective protection; for example, known anti-toxin vaccines must be given in multiple doses.

Childhood vaccination is commonplace and generally successful in developed countries, where there is ready access to health services and multiple immunizations (e.g. immunization against multiple pathogens and serial or multiple immunizations against a single pathogen) are possible. In the developing world, vaccination is far less common and far more problematic. For example, only about 20 percent of the 100 million children born in the developing world each year are vaccinated against diphtheria, pertussis, tetanus, measles, poliomyelitis and tuberculosis. It is estimated that each year, 5 million children in the developing world die and another 5 million children are physically or mentally disabled by these diseases, which could be prevented if adequate immunization were possible. Availability of effective vaccines which can confer long-term immunity with a single administration would, of course, be valuable in both developed and developing countries.

Vaccination of adults is also helpful in preventing many diseases in adults and, as is the case with children, in developing countries may prove to be difficult to carry out, particularly if multiple immunizations are necessary. Diseases such as leprosy, malaria, tuberculosis, and poliomyelitis, among others, have a high incidence among adults in Africa, Asia and Latin America and are the causes of thousands of deaths annually.

Much effort has been expended in developing vaccines against major diseases and, recently, consideration has been given to recombinant vaccine vehicles (e.g., genetically engineered viruses) to express foreign genes. For example, recombinant vaccinia virus, in which viral antigens are inserted into vaccinia virus—has been developed. For example, hepatitis B genes, influenza virus genes or DNA encoding rabies virus antigen have been spliced into vaccinia virus DNA in efforts to make vaccines. Panicali, D. et. al., *Proceedings of the National Academy of Sciences, USA*, 80: 5364–5368 (1983); Orr, T., *Genetic Engineering News*, p. 17, (March 1985); Paoletti, E. and D. Panicali, U.S. Pat. No. 4,603,112.

It is widely agreed, however, that such recombinant vaccinia virus would have at least two important drawbacks as a vaccine. First, there is a significant mortality and morbidity (1:100,000) associated with vaccinia virus, which is untreatable. Second, vaccination with recombinant vaccinia of individuals previously exposed to vaccinia virus has often failed to produce satisfactory immunization levels. Fenner, F., *New Approaches to Vaccine Development*, R. Bell and G. Torrigiani (ed.), Schwabe & Co., p. 187 (1984).

To date, vaccines have been developed which, although effective in many instances in inducing immunity against a given pathogen, must be administered more than once and may be unable to provide protection, on a long-term basis, against a pathogen. In addition, in many cases (e.g., leprosy, malaria, etc.), an effective vaccine has yet to be developed.

Mycobacteria

Mycobacteria represent major pathogens of man and animals. For example, tuberculosis is generally caused in humans by *Mycobacterium (M.) tuberculosis* and in cattle by *Mycobacterium (M.) bovis* (which can be transmitted to humans and other animals, in whom it causes tuberculosis). Tuberculosis remains widespread and is an important public health problem, particularly in developing countries. It is estimated that there are approximately 10 million cases of tuberculosis world-wide, with an annual mortality of 3 million. Joint International Union Against Tuberculosis and World Health Organization Study Group, *Tubercle*, 63:157–169 (1982).

Leprosy, which is caused by *M. leprae*, afflicts over 10 million people, primarily in developing countries. Bloom, B. R. and T. Godal, *Review of Infectious Diseases*, 5:657–679 (1984). *M. tuberculosis* and mycobacteria of the avium-intracellulare-scrofulaceum (MAIS) group represent major opportunistic pathogens of patients with acquired immunodeficiency disease (AIDS). Centers for Disease Control, *Morbidity and Mortality Weekly Report*, 34:774 (1986). *M. pseudotuberculosis* is a major pathogen of cattle.

On the other hand, Bacille Calmette-Guerin (BCG), an avirulent strain of *M. bovis*, is the most widely used human vaccine in the world and has been used as a live vaccine for more than 50 years. In the past 35 years, it has been administered to over 2.5 billion people, with remarkably few adverse effects (e.g., estimated mortality of 60/billion). BCG has been found in numerous studies to have protective efficacy against tuberculosis. Recently, however, it was found not to be effective in preventing pulmonary tuberculosis in Southern India. Tuberculosis Prevention Trial, Madras, *Indian Journal of Medical Research*, 72 (suppl.) :1–74 (1980).

Thus, although there are numerous vaccines available, including BCG, many are limited in value because they induce a limited immune response, must be given in multiple doses and/or have adverse side effects. In other cases (e.g., leprosy, malaria), a vaccine is simply unavailable. It would be of great value if a vaccine against a pathogen or pathogens of concern were available which provided long-term stimulation of immunity in recipients sufficient to provide protection against the pathogen(s) without adverse effects.

DISCLOSURE OF THE INVENTION

The present invention relates to genetically recombinant (genetically engineered) cultivable mycobacteria which express DNA of interest which has been incorporated into the mycobacteria, in which it is present in the mycobacterial genome or extrachromosomally, using genetic engineering techniques; to vectors useful for the introduction of DNA of interest into mycobacteria; to methods of introducing DNA into mycobacteria and to methods of incorporating or integrating DNA stably into the mycobacterial genome to produce genetically recombinant mycobacteria. It further relates to a method of transferring genetic material between different genera of microorganisms by means of genetically engineered shuttle vectors, which are shuttle phasmids or shuttle plasmids. These shuttle vectors, which are also the subject of the present invention, are useful for the transfer of genetic material between different genera of microorganisms and introduction of DNA of interest into mycobacteria.

Recombinant DNA vectors of the present invention are of two types: a temperate shuttle plasmid and a bacterial-mycobacterial shuttle plasmid (e.g., *E. coli* mycobacterial shuttle plasmid). Each type of recombinant vector can be used to introduce DNA of interest stably into mycobacteria, in which the DNA can then be expressed. In the case of the temperate shuttle plasmid, which includes DNA of interest, stable integration into the mycobacterial chromosomal or genomic DNA occurs via site specific integration. The DNA of interest is replicated as part of the chromosomal DNA. In the case of the bacterial-mycobacterial shuttle plasmid, which includes DNA of interest, the DNA of interest is stably maintained extrachromosomally as a plasmid (as a component of the plasmid). Expression of the DNA of interest occurs extrachromosomally as a plasmid (e.g., episomally). For example, a gene or genes of interest is/are cloned into a bacterial-mycobacterial plasmid and introduced into a cultivable mycobacterium, where it undergoes episomal replication (extrachromosomal replication). As a result of the work described herein, promoters which will express in mycobacteria have been defined; for example, the promoter expressing kanamycin resistance, the promoter expressing chloramphenicol resistance and the cI promoter have been shown to express in mycobacteria.

The recombinant vectors of the present invention are useful in the method of the present invention, by which genetic material can be transferred between different genera of microorganisms (e.g., between bacteria and mycobacteria). They have made it possible to introduce into mycobacteria, such as *Mycobacterium smegmatis (M. smegmatis)* and *Mycobacterium bovis*-BCG (BCG), DNA from another source (e.g., DNA from a source other than the mycobacterium into which the DNA is being incorporated—for example, *M. smegmatis* or BCG). The DNA from another source is referred to herein as DNA of interest. Such DNA of interest can be of any origin and is: 1) DNA which is all or a portion of a gene or genes encoding protein(s) or polypeptide(s) of interest; 2) DNA encoding a selectable marker or markers; or 3) DNA encoding both a selectable marker or markers and at least one protein or polypeptide of interest. The proteins or polypeptides of interest can be, for example, proteins or polypeptides against which an immune response is desired (antigen(s) of interest), enzymes, lymphokines, immunopotentiators, and reporter molecules of interest in a diagnostic context.

DNA of interest can be integrated or incorporated into the mycobacterial genome and is referred to as integrated DNA or integrated DNA of interest. As a result, DNA of interest can be introduced stably into and expressed in mycobacteria (i.e., production of foreign proteins is carried out from the DNA of interest present in the mycobacteria). Alternatively, DNA of interest is integrated into mycobacterial DNA, through the method of the present invention, as a result of homologous recombination. According to the method of the present invention, a recombinant plasmid is used for introduction of DNA of interest into mycobacterial cells and for stable integration of the DNA into the mycobacterial genome. The recombinant plasmid used includes: 1) mycobacterial sequences (referred to as plasmid-borne mycobacterial sequences) necessary for homologous recombination to occur (between plasmid-borne mycobacterial sequences and sequences in the mycobacterial genome); 2) DNA sequences necessary for replication and selection in *E. coli*; and 3) DNA of interest (e.g., DNA encoding a selectable marker and DNA encoding a protein or polypeptide of interest). The recombinant plasmid is introduced, using known techniques, into mycobacterial cells. The mycobacterial sequences in the plasmid can be identical to those present in the mycobacterial genome or sufficiently similar to those present in the mycobacterial genome to make homologous recombination possible. "Recognition" of homology of sequences present in the plasmid-borne mycobacterial DNA and identical of sufficiently similar sequences present in the mycobacterial genome results in crossover between the homologous regions of the incoming (plasmid-borne) mycobacterial DNA and the genomic mycobacterial DNA and integration of the recombinant plasmid into the mycobacterial genome. Integration occurs at a selected site in the mycobacterial genome which is non-essential, (i.e., not essential for mycobacterial replication). Integration of the homologous plasmid sequences is accompanied by integration of the DNA of interest into the mycobacterial genome.

The present invention further relates to recombinant mycobacteria which express DNA of interest which has been integrated into the mycobacterial DNA or which is maintained extrachromosomally as a plasmid. Such recombinant mycobacteria can be produced by introducing DNA of interest into any appropriate mycobacterium, such as *M. smegmatis*, *M. bovis*-BCG, *M. avium*, *M. phlei*, *M. fortuitum*, *M. lufu*, *M. paratuberculosis*, *M. habana*, *M. scrofulaceum* and *M. intracellulare*. In recombinant mycobacteria in which DNA of interest is integrated into genomic DNA, the DNA of interest is present in such a manner that 1) a mycobacterial gene is replaced (i.e., is no longer present in the mycobacterial genome) or 2) the DNA of interest is inserted into a mycobacterial gene, with the result a) that the mycobacterial gene is left intact and functional or b) that the mycobacterial gene is disrupted and rendered nonfunctional.

The resulting genetically recombinant mycobacteria (e.g., recombinant BCG, recombinant *M. smegmatis*) are particularly useful as vehicles by which the DNA of interest can be expressed. These are referred to as genetically recombinant mycobacteria or mycobacterial expression vehicles. Such vehicles can be used, for example, as vaccine vehicles which express a polypeptide or a protein of interest (or more than one polypeptide or protein), such as an antigen or antigens, for one or more pathogens of interest. The recombinant mycobacteria can also be used as a vehicle for expression of immunopotentiators, enzymes, pharmacologic agents and antitumor agents; for expression of a polypeptide or a protein useful in producing an anti-fertility vaccine vehicle; or for expression of stress proteins, which can be administered to evoke an immune response or to induce tolerance in an autoimmune disease (e.g., rheumatoid arthritis). Recombinant mycobacteria can, for example, express protein(s) or polypeptide(s) which are growth inhibitors or are cytocidal for tumor cells (e.g., interferon α, β or γ; interleukins 1–7, tumor necrosis factor (TNF) α or β) and, thus, provide the basis for a new strategy for treating certain human cancers (e.g., bladder cancer, melanomas). Pathogens of interest include any virus, microorganism, or other organism or substance (e.g., a toxin or toxoid) which causes disease. The present invention also relates to methods of vaccinating a host with the recombinant mycobacterium to elicit protective immunity in the host. The recombinant vaccine can be used to produce humoral antibody immunity, cellular immunity (including helper and cytotoxic immunity) and/or mucosal or secretory immunity. In addition, the present invention relates to use of the antigens expressed by the recombinant cultivable mycobacterium as vaccines or as diagnostic reagents.

The vaccine of the subject invention has important advantages over presently-available vaccines. First, mycobacteria have adjuvant properties among the best currently known and, thus, stimulate a recipient's immune system to respond to other antigens with great effectiveness. This is a articularly valuable aspect of the vaccine because it induces cell-mediated immunity and will, thus, be especially useful in providing immunity against pathogens in cases where cell-mediated immunity appears to be critical for resistance. Second, the mycobacterium stimulates long-term memory or immunity. As a result, a single (one-time) inoculation can be used to produce long-term sensitization to protein antigens. Using the vaccine vehicle of the present invention, it is possible to prime long-lasting T cell memory, which stimulates secondary antibody responses neutralizing to the infectious agent or the toxin. This is useful, for example, against tetanus and diphtheria toxins, pertussis, malaria, influenza, herpes viruses and snake venoms.

BCG in particular has important advantages as a vaccine vehicle in that: 1) it is the only childhood vaccine currently given at birth; 2) in the past 40 years, it has had a very low incidence of adverse effects, when given as a vaccine against tuberculosis; and 3) it can be used repeatedly in an individual (e.g., in multiple forms).

A further advantage of BCG in particular, as well as mycobacteria in general, is the large size of its genome (approximately $3 \times 10^6$ bp in length). Because the genome is large, it is able to accommodate a large amount of DNA from another source (i.e., DNA of interest) and, thus, can be used to make a multi-vaccine vehicle (i.e., one carrying DNA of interest encoding protective antigens for more than one pathogen).

BRIEF DESCRIPTION OF THE DRAWINGS

FIG. 3A shows agarose gel of mycobacteriophage TM4 DNA and shuttle plasmid phAE1 DNAs digested with KpnI. Lane 1 contains lambda DNA digested with Hind III; lanes 2 and 3 contain TM4 DNA that was unligated (lane 2) or ligated (lane 3) prior to digestion cut with KpnI; lanes 4 and 5 contain phAE1 DNA isolated from phage particles propagated on *M. smegmatis* (lane 4) and phAE1 isolated from *E. coli* cells as a plasmid (lane 5). Note that the arrows point to the 2.1 Kb and the 1.8 Kb fragments that form a 3.9 Kb fragment when ligated at the cohesive ends.

FIG. 3B shows results of a Southern blot analysis of plasmid phAE1, using pHC79 as a probe (panel B). The autoradiograph of FIG. 3A is shown after blotting onto a Biotrans nylon membrane (ICN) and probing with pHC79 DNA that had been nick-translated with $^{32}$P-dCTP.

FIG. 4A shows lysis of BCG by the phages. Titres of phage (pfu/ml) used at $10^{-1}$ dilution were: DS6a, $2\times10^6$ on *M. tuberculosis*, H37Ra; 33D, $2\times10^6$ on *M. smegmatis*, mc²6; TM4, $3\times10^8$ on mc₂6; and phAE1, $3\times10^8$ on mc²6. Dilutions of phages (5 ul) were spotted on a soft agar overlay containing $10^8$ BCG cells. Resulting lysis was photographed after incubation for 10 days at 37° C.

FIG. 4B shows the presence of cosmid DNA in phAE1. Plaque lifts on these plates were carried out as described below and hybridized with $^{32}$P-labelled pHC79 DNA; this was followed by autoradiography.

FIG. 4C is an electron micrograph of shuttle plasmid phAE1 phage particles. Phage particles that had been purified on CsCl gradients were placed on carbon coated, Parloidon-coated grids, blotted and washed with one drop of 1% phosphotungstic acid. Electron micrographs were taken using a JEOL 1200EX electron microscope at 80 kV, 30,000×.

FIG. 12A is a schematic representation of selection, using growth on kanamycin-containing medium, of mycobacterial cells in which the PyrF gene containing the Kan gene is present. FIG. 12B is a schematic representation of selection, using growth on fluoro-orotic acid-containing medium, of mycobacterial cells having the PyrF gene containing the Kan gene integrated into genomic DNA.

FIG. 17 shows results of Western blot analysis showing expression of the *M. leprae* gene encoding stress-induced 65 kD antigen in *M. smegmatis* and BCG.

DETAILED DESCRIPTION OF THE INVENTION

Figure 1:
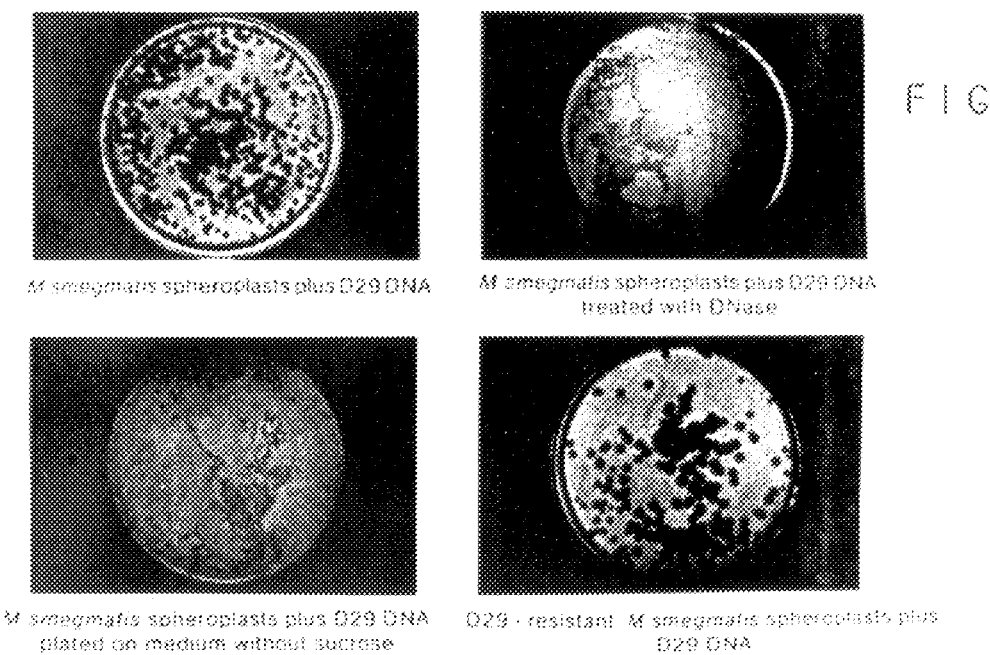
FIG. 1 shows results of transfection of *Mycobacterium smegmatis* spheroplasts with mycobacteriophage D29 DNA.

*Mycobacterium bovis*-BCG (BCG or *M. bovis*-BCG) is an avirulent *M. bovis* derivative which is widely used throughout the world and is commonly used to provide protection against tuberculosis, although its effectiveness has recently been called into question. *Mycobacterium smegmatis* is a nonpathogenic bacillus which shares antigenic and adjuvant properties with BCG. Both are also reasonably easy to grow in culture.

Because both mycobacteria have excellent adjuvant activity for induction of cell-mediated immunity, stimulate long-term memory (immunity) and have a low mortality associated with their use, they are excellent candidates as recombinant vaccines. That is, they are excellent candidates for use as vehicles (vaccine vehicles) into which genetic material (DNA) of interest (DNA from a source other than the mycobacterium into which it is being introduced) can be inserted and subsequently expressed.

DNA of interest can be of any origin and is: 1) DNA which is all or a portion of a gene or genes encoding protein(s) or polypeptide(s) of interest; 2) DNA encoding a selectable marker or markers; or 3) DNA encoding both a selectable marker (or selectable markers) at least one protein or polypeptide of interest. The term polypeptide of interest, used herein, includes all or a portion of a protein to be expressed. Such DNA of interest is expressed in the genetically recombinant mycobacteria, in which it is present in (integrated into) the mycobacterial genome or is present extrachromosomally. Incorporated DNA, as defined herein, includes DNA present in chromosomal DNA or present in mycobacteria extrachromosomally (episomally). DNA is incorporated by means of a shuttle plasmid or shuttle plasmid, resulting in integration into mycobacterial chromosomal or genomic DNA or the presence of DNA of interest episomally (extrachromosomally). Integration of DNA of interest can occur by homologous or nonhomologous recombination, such as site-specific recombination of a phage-encoded system or recombination mediated by a transposable element.

Until the present time it has not been possible to transform a mycobacterium through the use of plasmid DNA. Further, until now, it has not been possible to produce recombinant mycobacterial vaccine vehicles in which DNA encoding a polypeptide or protein such as one against which an immune response is desired, is stably integrated, at selected sites and in selected orientations, in genomic DNA.

A principal objective of work on the development of a recombinant mycobacterium to be used as an expression vehicle or a vaccine vechicle is the introduction into the mycobacterium of DNA vectors that direct the expression of DNA encoding a product or products, such as a protein or polypeptide, important for protection against one or more pathogens. It is now possible, using the method and the shuttle or plasmid vector of the present invention, to incorporate DNA of interest into a cultivable mycobacterium (e.g., into the mycobacterial genome or into the mycobacterium in such a manner that it is expressed extrachomosomally).

The shuttle plasmid vector of the present invention is unique in that it replicates as a plasmid in bacteria and as a phage in mycobacteria. In a particular embodiment, the shuttle plasmid vector, which is referred to as a shuttle plasmid, includes two species of specific cohesive end (or cos sites): one for lambda phage, which functions in $E.$ $coli$; and one for mycobacteria (e.g., the mycobacteriophage TM), which functions in mycobacteria. That is, it contains two sets of cohesive ends. Because it contains one set for lambda and one for mycobacteria, it can be incorporated into both. The presence of the lambda COS sequence also makes it possible to use the efficient technique of cosmid cloning, which utilizes the lambda in vitro packaging system for efficient cloning of large DNA molecules into $E.$ $coli$. Further, the shuttle vector has a unique EcoRI site into which antigen-encoding DNA can be inserted. Thus, the shuttle vectors have made it possible to develop a transfection system which permits introduction of recombinant DNA molecules into mycobacteria.

There are several means by which genetic material of interest can be incorporated into mycobacteria to produce recombinant mycobacteria of the present invention. For example, DNA of interest can be stably introduced (e.g., integrated into the mycobacterial chromosome) into mycobacterial cells by cloning into a shuttle plasmid, particularly a temperate shuttle plasmid (e.g., a phage capable of lysogenizing a cell). Introduction of DNA of interest in this manner results in integration of the DNA into the mycobacterial chromosome.

For example, an $E.$ $coli$ cosmid was introduced into the temperate mycobacteriophage L1, producing shuttle phasmids capable of replicating as plasmids in $E.$ $coli$ or lysogenizing the mycobacterial host. These temperate shuttle phasmids form turbid plaques on $M.$ $smegmatis$ and, upon lysogenization, confer resistance to superinfection and integrate within the mycobacterial chromosome. When an L1-shuttle plasmid containing a cloned gene conferring kanamycin-resistance in $E.$ $coli$ was introduced into $M.$ $smegmatis$, stable kanamycin-resistant colonies (i.e., lysogens) were obtained.

Alternatively, a plasmid vector can be used to introduce DNA of interest into mycobacteria, in which the DNA is expressed extrachromosomally. For example, the shuttle plasmid $M.$ $fortuitum$::$E.$ $coli$ hybrid plasmids were constructed from mycobacterial and $E.$ $coli$ replicons which contain kanamycin- and chloramphenicol-resistance genes. When introduced into $M.$ $smegmatis$ or BCG by electroporation, these shuttle plasmids conferred stable kanamycin- and chloramphenicol-resistance upon transformants. Thus, the vectors have made it possible to develop a transfection system which permits introduction of recombinant DNA molecules into mycobacteria.

It is also possible to introduce DNA of interest and cause it to integrate into host chromosomes without a phage. For example, this can be accomplished by homologous recombination, site specific recombination or nonhomologous recombination (e.g., by means of a transposon, which results in random insertion into host chromosomal material). Homologous recombination has been used, as described below, to integrate DNA of interest (e.g., kanamycin-resistance gene, 65 KD $M.$ $leprae$ gene).

In order to successfully introduce DNA of interest into a mycobacterium or into the mycobacterial genome by means of the shuttle vector or plasmid vector of the present invention or by homologous recombination, the following general approaches were followed. Although it is described in terms of $M.$ $smegmatis$ and $M.$ $bovis$-BCG, it is to be understood that it can also be used to introduce DNA of interest into other mycobacteria and that these other genetically recombinant mycobacteria can also be expression or vaccine vehicles. Such other mycobacteria include: $M.$ $smegmatis$, $M.$ $bovis$-BCG, $M.$ $avium$, $M.$ $phlei$, $M.$ $fortuitum$, $M.$ $lufu$, $M.$ $paratuberculosis$, $M.$ $habana$, $M.$ $scrofulaceum$, and $M.$ $intracellulare$. In the case of slow growing mycobacteria (e.g., $M.$ $bovis$-BCG and $M.$ $tuberculosis$) to be used as vaccine vehicles, it is particularly valuable to go through (i.e., introduce DNA encoding an antigen or antigens of interest into) $M.$ $smegmatis$ and, subsequently, into $M.$ $bovis$-BCG.

Development of a shuttle vector to transfer DNA into mycobacteria

Transfection of mycobacteriophage DNA into $M.$ $smegmatis$

To develop a system that permits manipulation of DNA in mycobacteria, it was first necessary to develop an efficient means of transferring DNA into the bacillus. The technology used was a modification of that described by Okanishi and Hopwood in relation to the preparation of spheroplasts for Streptomyces. Streptomyces, like mycobacteria, are $Actinomycetales$. Okanishi, M. et al., $Microbiology$, 80: 389–400 (1974); Hopwood, D. A. and H. M. Wright, $Molecular$ $Genetics$, 162: 307–317 (1978). The modified technique was used in combination with the addition of polyethylene glycol to facilitate entry of DNA molecules into bacterial spheroplasts.

Because of the unavailability of useful selectable antibiotic resistance markers in plasmids for transforming mycobacteria, the system chosen to evaluate optimum conditions for DNA transfer into mycobacteria was the transfection of DNA from lytic mycobacteriophages. Two advantages of such a system are that results obtained were quantitative and readily visualized as plaques within 24 hours.

Transfection of mycobacteriophage DNA into *M. smegmatis* is described in detail in Example 1. Briefly, DNA was initially introduced into mycobacteria having all or a portion of the cell walls removed (i.e., protoplasts or spheroplasts), using polyethylene glycol. Transfection experiments were initiated with DNA from mycobacteriophage D29, which propagates on a wide variety of mycobacteria and forms large clear plaques on *M. smegmatis*. Plate lysates of D29 phage prepared on *M. smegmatis* consistently yielded greater than $10^{11}$ pfu (plaque forming units) per ml of lysate. The harvested phages were twice purified on CsCl equilibrium gradients; they banded at an equilibrium buoyant density of 1.51. Phage DNA was extracted by proteinase K treatment and phenol-chloroform extraction. Restriction analysis of ligated and unligated D29 DNA demonstrated that the phage genomic DNA was double stranded, 50 kb in size, and possessed cohesive ends.

The results of transfection of *M. smegmatis* spheroplasts by mycobacteriophage D29 DNA are illustrated in FIG. 1. Efficiencies of $10^3$ to $10^4$ pfu per ug D29 DNA were obtained, thus demonstrating the first efficient transfection system for mycobacteria. That these plaques were the result of transfection of *M. smegmatis* spheroplasts was demonstrated by the following: (i) transfection was abolished by DNase; (ii) osmotic shock of treated cells prevented productive transfection; and (iii) spheroplasts derived from a D29 phage-resistant mutant of *M. smegmatis* were transfected at frequencies comparable to the parent strain. Further refinement of these techniques made it possible to obtain frequencies greater than $10^5$ pfu per ug of D29 DNA.

Introduction of DNA of interest into mycobacteria

A vector that would permit both the manipulation and amplification of mycobacterial DNA constructs in *E. coli*, and subsequent transfer into and replication in mycobacteria was developed. In particular, it was highly desirable to have the capability of introducing DNA of interest into fast-growing non-pathogenic mycobacterium (e.g., *M. smegmatis*), as well as into slow-growing mycobacteria (e.g., *M. bovis*-BCG and *M. tuberculosis*). Although plasmids have been found in some mycobacterial strains within the MAIS complex and in *M. fortuitum*, none have yet been described which replicate within *M. smegmatis, M. bovis*-BCG, or *M. tuberculosis*. With one exception, none of these plasmid possess selectable markers. Crawford, J. T. and J. H. Bates *Infections and Immunity,* 24: 979–981 (1979); Mizuguchi, Y. et al., *Journal of Bacteriology,* 146: 656–659 (1981); Meissner, P. S. and J. O. Falkinham, *Journal of Bacteriology,* 157: 669–672 (1984). In contrast, a variety of phages that replicate in *M. smegmatis, M. bovis*-BCG, and *M. tuberculosis* have been described and used for typing isolates.

The strategy used was to construct a vector which replicates as a plasmid in *E. coli* and as a phage in mycobacteria. One approach to accomplishing this development of a shuttle plasmid was based on the idea that since mycobacterial DNA is not expressed well in *E. coli*, it should be possible to clone, in a plasmid vector, a functional mycobacteriophage genome which would not lyse the *E. coli* host. It would, thus, be able to replicate in both types of organisms. Because transfection of *M. smegmatis* would yield mycobacteriophage particles, introduction of DNA of interest into the slow growing mycobacteria (e.g., BCG) could be achieved by phage infection. A bifunctional vector for Streptomyces has been described by Suarez and Chater. Suarez, J. E. and K. F. Chater, *Nature,* 286: 527–529 (1980). A lambda-ColE1 vector with dual properties in *E. coli* has been referred to by Brenner and co-workers as a plasmid. Brenner, S. et al., *Gene,* 17: 27–44 (1982).

For this purpose, the mycobacteriophage TM4 was used. TM4 has been reported to be a lysogenic phage isolated from *M. avium.* Timme, T. L. and P. J. Brennan, *Journal of General Microbiology,* 130: 205–209 (1984). It had been characterized as being a phage that lysogenizes *M. smegmatis*. It was shown to be capable of replicating in *M. smegmatis*, BCG, and *M. tuberculosis* and has been reported to be temperate. This phage also has a double stranded DNA genome of 50 kb and possesses cohesive ends. It is possible, however, to use other mycobacteriophages having similar characteristics. The following procedures described as used with TM4 can also be used with such other mycobacteriophages in constructing a vector.

Figure 2:
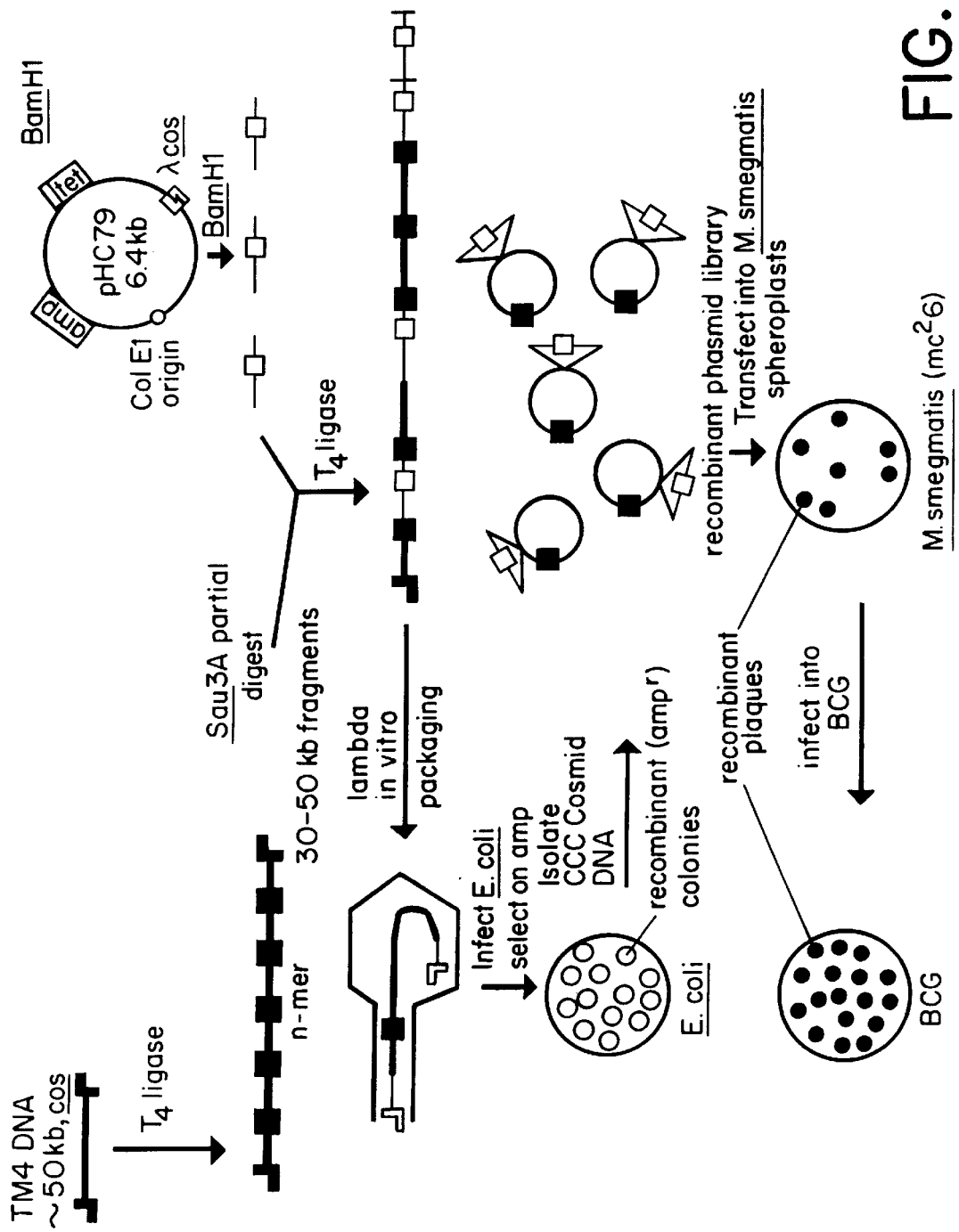
FIG. 2 is a schematic representation of the construction of the shuttle plasmid, phAE1.

The strategy used to introduce an *E. coli* plasmid replicon into phage TM4 to generate a vector that replicates in *E. coli* as a plasmid and in mycobacteria as a phage is schematized in FIG. 2. Plate stock lysates and genomic DNA of TM4 phage were prepared as described for D29 phage (see Example 1). TM4 DNA was ligated at high concentrations to form long concatamers of annealed cohesive ends. The ligated DNA was partially digested with Sau3A. Sau3A cuts the TM4 genome frequently (e.g., an average of once every 300 bp) to fragments 30–50 kb in size. It generates a set of DNA fragments whose lengths were that of the entire TM4 genome or TM4 genomes with small deletions, but are cleaved at any of the Sau3A sites within the genome. These DNA fragments were ligated to the 6.5 kb cosmid pHC79, which contains the gene for resistance to ampicillin and had been cleaved with BamHI. Hohn, B. and J. Collins, *Gene,* 9: 291–298 (1980). To select for recombinant molecules of the appropriate size, the ligation mixture was packaged into bacteriophage lambda heads in vitro. This selects for DNA fragments which contain lambda COS sites and are between 38 and 53 kb in size. The resulting phage particles were transduced into *E. coli* and colonies containing pHC79::TM4 DNA molecules were selected on media containing ampicillin. Plasmid covalently closed circular DNA was isolated from 40,000 pooled ampicillin-resistant ($amp^r$) colonies. Birnboim, H. and Doly, *Journal of Nucleic Acid Research,* 7: 1513–1525 (1979).

This library contains recombinant molecules of TM4 genomes into which pHC79 cosmid DNA had been randomly inserted in Sau3A sites around the TM4 genome. It was transfected into *M. smegmatis* spheroplasts to select for TM4 phages which had pHC79 inserted in non-essential regions. Such phages were, thus, shuttle phasmids. The transfection yielded 100 plaque forming units (pfu) per ug of plasmid DNA. Plaque lifts were used to screen for hybridization to $^{32}$P-labelled pHC79.DNA; only 10 of 4000 plaques hybridized to the labelled pHC79.

Following plaque purification and propagation on *M. smegmatis* cells, one such phage was studied in detail and designated as plasmid, phAE1. Plasmid phAE1 has been deposited (Feb. 26; 1986), according to the terms of the Budapest Treaty, at the American Type Culture Collection (Rockville, Md.) under accession number 40306. All restrictions on public access to the deposit will be removed irrevocably upon grant of a United States patent based on this application. DNA was isolated from phAE1 phage particles grown on *M. smegmatis*, purified on CsCl gradients, ligated to form concatamers, and packaged in vitro into bacteriophage lambda heads. The resulting particles transferred ampicillin resistance to *E. coli* cells and, when transfected, produced plaques on *M. smegmatis*. This was proof that phAE1 functions as a shuttle vector.

Figure 3A:
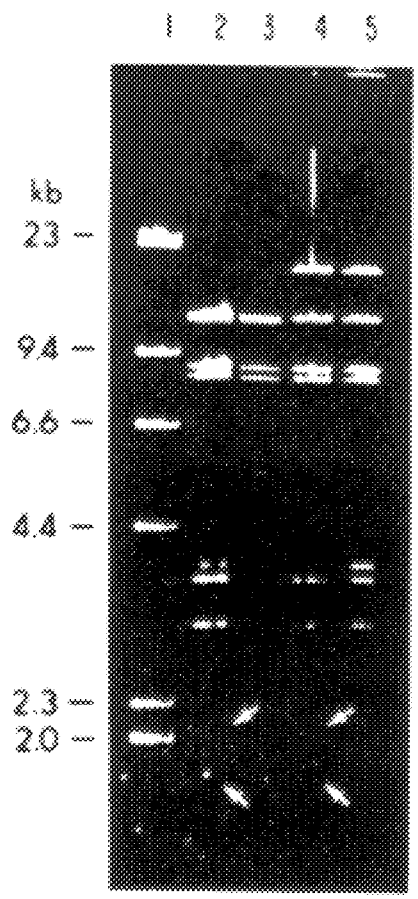
FIGS. 3A and 3B shows results of assessment of shuttle plasmid phAE1.
Figure 3B:
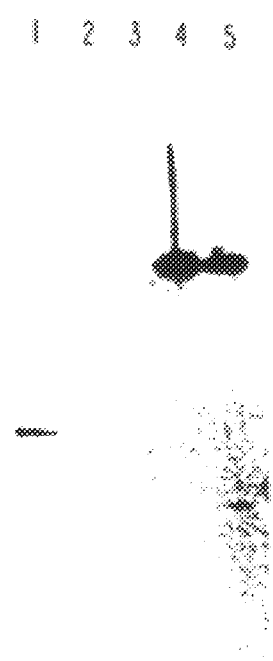
Figure 4A:
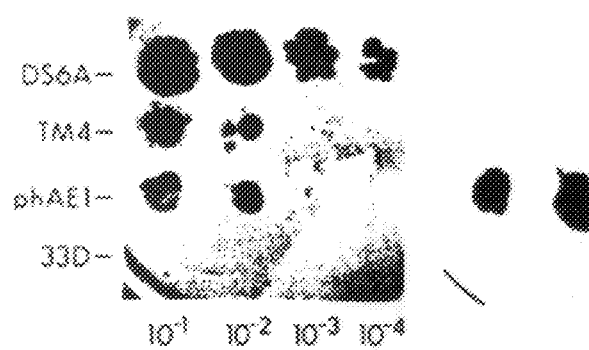
FIGS. 4A–4C shows replication of phAE1 on BCG. It compares lysis of the Glaxo vaccine strain of BCG by DS6A, which is a mycobacteriophage known to plaque on *M. tuberculosis* and BCG, but not on other mycobacteria; phage 33D, known to plaque on *M. smegmatis* and not BCG; and phage TM4, which plaques on both species.
Figure 4B:
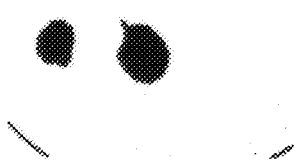
Figure 4C:
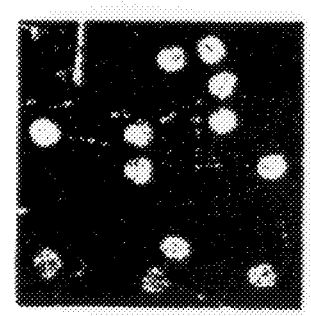
Figure 5A:
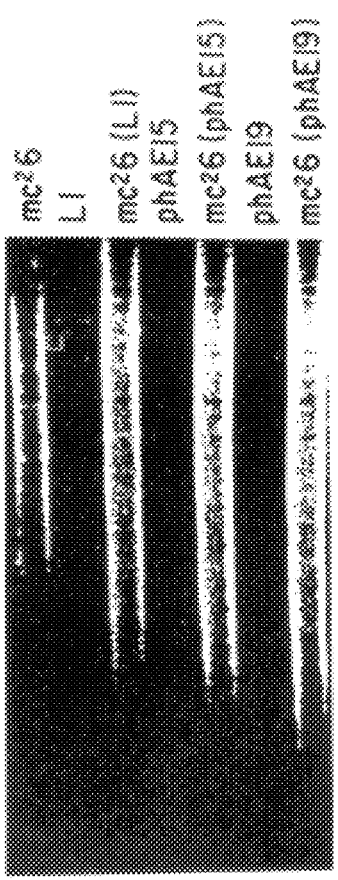
FIG. 5 shows integration of mycobacteriophage L1 and L1-shuttle plasmid DNA into the *M. smegmatis* chromosome. DNAs from phage L1 and L1-shuttle phasmids and chromosomal DNAs from corresponding lysogens were digested with BamHI and electrophoresed in agarose. Panel A shows an ethidium bromide stained gel. Panel B shows the autoradiograph of the Southern analysis of this gel probed with $^{32}$P-labelled phage L1 DNA. The following are shown in the lane indicated: phage DNA from the parent phage L1 (lane 2), from shuttle plasmid phAE15 (lane 4) and from shuttle plasmid phAE19 containing the aph gene (lane 6); bacterial chromosomal DNA from the parent *M. smegmatis* strain (lane 1), from that strain lysogenized with L1 (lane 3), with phAE15 (lane 5), and with phAE19 (lane 7). L1, phAE15, and phAE19 have integrated site-specifically within the chromosome of their respective lysogens (Panel B, lanes 3, 5 & 7), as evidenced by the predominant loss of a single 6.7 kb band present in each phage (note square in L1, lane 2) and the appearance of two new bands, 9.0 kb and 1.7 kb, in each lysogen (circles).
Figure 5B:
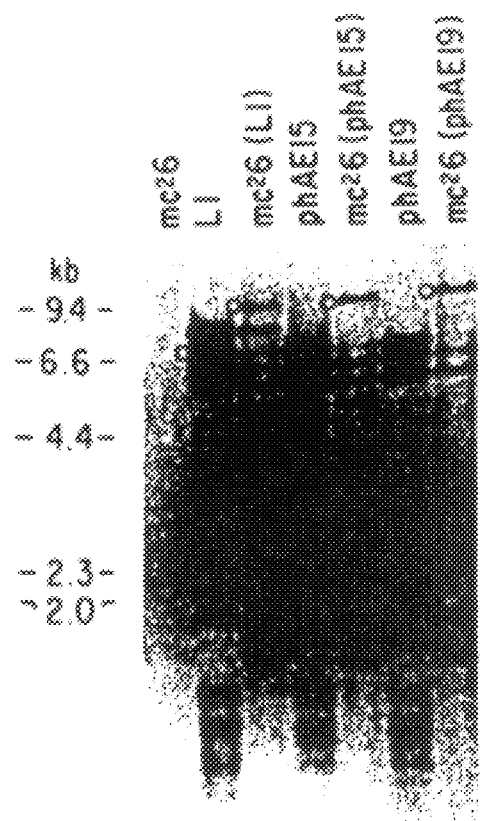
Figure 6:
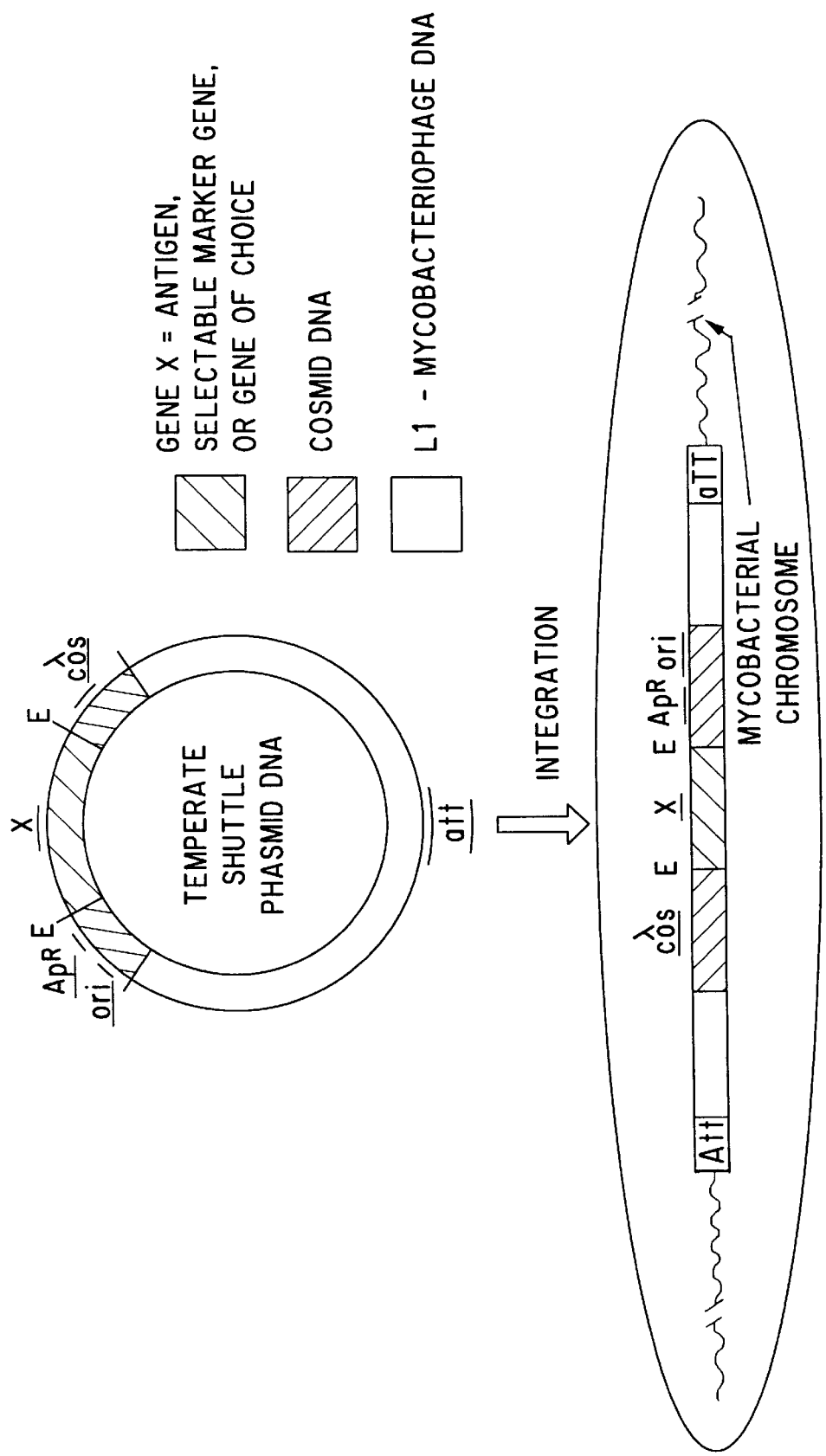
FIG. 6 is a schematic representation of the use of temperate shuttle phasmids as cloning vectors to stably introduce DNA of interest into the mycobacterial chromosome. DNA of interest (designated GENE X) can be inserted into unique restriction sites in shuttle plasmid DNA and subsequently introduced into mycobacteria. In mycobacteria, the shuttle plasmid, carrying the DNA of interest, can lysogenize and be maintained stably as a prophage.

Restriction digests of phAE1 DNA isolated from phage particles propagated on *M. smegmatis* and of phAE1 DNA isolated as plasmid DNA isolated from *E. coli* showed identical patterns, except for the presence of unannealled fragments held together by the cohesive ends seen in the phage DNA preparation (FIG. 3A). Southern analysis demonstrated that the cosmid pHC79 was cloned within one of the two 11 kb KpnI restriction fragments of the TM4 genome (FIG. 3B). By electron microscopy, the phAE1 particles resemble bacteriophage lambda with hexagonal heads that average 50 um in diameter. However, these particles have long tails (180 to 220 um in length) with a disc-like baseplate present on many of the tails (FIG. 4C). The structure is very similar to that of the parent TM4 phage. Timme, T. L. and P. J. Brennan, *Journal of Gen. Microbiology*, 130: 205–209 (1984).

Restriction analysis of DNAs from isolated phages resulting from the transfection of the pHC79::TM4 library into *M. smegmatis* that did not hybridize to pHC79 showed them to be identical. The phage appears to have resulted from a recombination event which occurred in transfected cells containing two or more pHC79::TM4 molecules, yielding a wild-type TM4 genome.

Of particular interest is the observation that the shuttle plasmid, phAE1, which was obtained from *M. smegmatis*, is like its parent TM4 in that it is able to infect and replicate in three different *M. bovis*-BCG vaccine strains tested: the Glaxo, Pasteur, and Danish BCGs. These results are presented in FIGS. 4A and 4B.

Thus, this demonstrates successful construction of *E. coli*-mycobacterial shuttle phasmids that are recombinant DNA molecules that not only have the ability to replicate in *E. coli* as plasmids and in mycobacteria as phages, but also have the ability to be packaged into bacteriophage lambda heads or into mycobacteriophage particles. It also demonstrates that recombinant DNA has been introduced into both a fast-growing mycobacterium (*M. smegmatis*) and a slow-growing mycobacterium (*M. bovis*-BCG). This makes it possible to infect BCG vaccine strains with the shuttle phasmids and, thus, to introduce cloned genes into mycobacteria. Thus, this eliminates the need to develop a transfection system for BCG. That is, because the *E. coli*-mycobacterial shuttle plasmid, upon transfection into mycobacteria is packaged into mycobacterial particles, DNA of interest can be introduced into slow-growing mycobacteria (e.g., BCG) by transduction, rather than transfection. Until now, this could not be done and this advance makes it possible to produce recombinant mycobacterial vaccine vehicles, which can be used to immunize against one or more antigens of interest.

The use of in vitro packaging to construct these phasmids can be extended as an efficient strategy for cloning of genes (e.g., genes, or DNA of interest, encoding an antigen or antigens for one or more pathogens against which an immune response is desired) into these vectors, as long as the size limits of the packaging system are not exceeded. It is also possible, by screening additional TM4::pHC79 recombinant phasmids, to determine the maximum amount of DNA that can be deleted from the TM4 phage and to define additional non-essential regions of the phage genome into which DNA can be inserted.

Introduction of new genes (e.g., DNA of interest encoding antigens) into mycobacteria by means of the shuttle plasmid entails cloning DNA fragments into the shuttle plasmid in *E. coli* and subsequently transfecting them into *M. smegmatis* spheroplasts. This yields recombinant phage particles containing the cloned gene(s). Using the resulting *M. smegmatis* spheroplasts containing the recombinant phages, it is possible to infect BCG with high efficiency (approaching 100% efficiency), thus introducing DNA of interest included in the recombinant phages into BCG. Development of conditions for establishing lysogeny or recombination, to permit stable expression of the foreign gene(s) in mycobacterial cells, is highly desirable.

Introduction of DNA of interest into mycobacterial cells

The shuttle vectors described above and in the following sections can be used to introduce DNA of interest which encodes one or more antigens for one or more pathogens of interest into mycobacteria, such as *M. bovis*-BCG or *M. smegmatis*. It can also be used, by introducing DNA encoding appropriate antigens, such as human gonadotropin hormone (HGH) fragments, into mycobacteria, to produce an anti-fertility "vaccine." These vectors can also be used to introduce DNA encoding a protein or a polypeptide which is a growth inhibitor for or cytocidal to tumor cells. The resulting recombinant mycobacteria can be used, respectively, to non-specifically augment immune responses to foreign antigens expressed in mycobacteria and to treat some human cancers. The shuttle vectors provide a means of manipulating and amplifying recombinant DNA constructs in a bacterium (e.g., *E. coli*, Streptomyces, Bacillus), or other organism (e.g., yeast), and subsequently transfering them into a mycobacterium where the DNA is expressed.

As a result, it is possible to produce recombinant mycobacterial vaccines which can be used to immunize individuals against, for example, leprosy, tuberculosis, malaria, diphtheria, tetanus, leishmania, salmonella, schistomiasis, measles, mumps, herpes, and influenza. Genes encoding one or more protective antigens for one or more of the disease-causing pathogens can be introduced into the mycobacterium. Of particular value is the ability to introduce genes encoding antigens of pathogens which require T-cell memory or effector function. Administration of the resulting recombinant mycobacterial vaccine to a host results in stimulation of the host's immune system to produce a protective immune response.

A vaccine against a pathogen or toxin can be produced, using the shuttle plasmid of the present invention, by the following procedure: DNA encoding an antigen (or antigens) for the pathogen or toxin against which protection is desired is obtained. The DNA can be obtained by isolation of the naturally-occurring DNA (e.g., from the pathogenic organism or toxin-producing organism); by cloning and amplification of the DNA sequence of interest, using known genetic engineering techniques (See, for example, Maniatis, T. et. al. Molecular Cloning: A Laboratory Manual, Cold Spring Harbor, N.Y. (1982).); or by mechanical synthesis.

By the following procedure, the gene or genes of interest (i.e., which encode one or more antigens against which immunity is desired) are cloned into the shuttle plasmid. This can be explained with reference to FIG. 2, which is a schematic representation of the shuttle plasmid phAE1. The cohesive ends of the shuttle plasmid are ligated, using known techniques. The resulting shuttle plasmid material is cut (digested) with a unique restriction enzyme (e.g., a restriction enzyme which cuts at unique sites, such as EcoRI and EcoRV, in the shuttle plasmid). An alternative approach to cuts made in this way is the addition (by ligation) of a polylinker (oligonucleotide sequence) which is useful with (can be cut by) other restriction enzymes. In this case, the linker is cut open with a selected restriction enzyme, producing sites at which DNA of interest can be inserted.

In the first case (cutting using a unique restriction enzyme), the result is shuttle plasmid molecules which have been cut once and into which DNA of interest can be inserted. In the second case, there is also at least one site at which DNA can be inserted. An antibiotic-resistance-encoding gene (e.g., an ampicillin-resistance-encoding gene) and DNA encoding one or more antigens, against which immunity is desired, can be ligated, using known techniques, at the restriction sites. The DNA being inserted and the shuttle plasmid DNA are generally ligated in equal molar amounts.

The resulting ligated DNA, which in this case includes the shuttle plasmid DNA, an antibiotic resistance gene and antigen-encoding DNA, is packaged into bacteriophage lambda heads using lambda in vitro packaging mix. E. coli is subsequently transduced with the phage, with the result that it is possible to screen (using antibiotic-containing medium) for colonies containing the antibiotic-resistance-encoding gene and the antigen-encoding DNA.

The resulting "library" is introduced into M. smegmatis using, for example, electroporation. Plaques which contain shuttle phasmids containing cloned insert DNA are selected. Subsequently, recombinant M. smegmatis can be used to infect a cultivable mycobacterium, such as BCG, with high efficiency. As a result, the antigen-encoding DNA is introduced into mycobacterial genomic DNA, where it will be expressed.

Selection of BCG containing the DNA of interest (here DNA encoding one or more antigens integrated into their genomic DNA) can be carried out using a selectable marker. One approach to selection of BCG containing DNA encoding one or more antigens, introduced by infection with the recombinant phage, is based on use of a selectable marker, which is an antibiotic resistance gene. In this case, the shuttle plasmid includes a gene encoding, for example, kanamycin resistance, viomycin resistance, thiostrepton resistance, hygromycin resistance, or bleomycin resistance.

A second approach in which a selectable marker is used to select BGG containing the DNA of interest is an auxotrophy strategy (i.e., one which relies on use of a mutant microorganism which requires some nutrient or substance not required by the organism from which the mutant was derived). In this case, a mycobacterium having the mutation is used and the gene which encodes the missing or mutated function is incorporated into the shuttle plasmid (which also contains antigen-encoding DNA). Selection for mycobacteria containing the antigen-encoding DNA is thus based on the ability of mycobacteria into which the shuttle plasmid is successfully introduced to survive, when grown on appropriate media.

For example, a system which includes a host mutant (e.g., M. smegmatis, BCG) and a selectable marker that complements the mutation can be used. Such a system can include a host mutant which is a pyrF$^-$BCG mutant and a selectable marker, such as a pyrF$^+$ gene, present in the plasmid shuttle vector used to introduce the antigen-encoding DNA into the (mutant) BCG. For example, the plasmid can include, in addition to the antigen-encoding DNA inserted into cosmid DNA, the pyrF$^+$ gene. Thus, BCG mutants into which the plasmid is introduced by infection can be selected by plating on minimal media. An alternative approach is to use 2-deoxyglucose-resistant mutants; in this case, the mycobacterial glucokinase gene is cloned into the plasmid and is used for selection, as described above for pyrF.

Selection on this basis will result in BCG having the antigen-encoding DNA stably integrated into genomic DNA and expressed by the bacillus. For this, gene expression signals (e.g., promoters, ribosome binding sites) are included upstream of the foreign (antigen-encoding) DNA, to enable BCG containing the antigen-encoding DNA to express it at levels sufficient to induce an immune response in a host to whom it is administered.

It is also possible to select BCG containing DNA encoding one or more antigens by use of monoclonal antibodies. In this case, a gene or gene fragment encoding one or more epitopes of an antigen (e.g., M. leprae or M. tuberculosis) for which monoclonal antibodies are available is introduced into the mycobacteria. Such monoclonal antibodies are used to select for recombinant BCG containing a gene or genes encoding one or more of these epitopes. The antigen genes introduced in this way contain a promoter sequence and other regulatory sequences. As a result, additional series (e.g., DNA encoding other antigens) can be added, using genetic engineering techniques, in frame, such that recombinant BCG identified by monoclonal antibodies to one antigen would also be expressing other foreign antigen-encoding DNA so introduced.

A parallel strategy which makes use of a plasmid to introduce antigen-encoding DNA into cultivable mycobacteria can also be used to make a vaccine vehicle. This will result in stable maintenance of the DNA of interest extra-chromosomally as a plasmid and its subsequent expression. Construction of such a shuttle plasmid is represented schematically in FIG. 8. In this case, a selectable marker, which would make it possible to select cells containing the antigen-encoding DNA, is used. The selectable marker can be, for example, an antibiotic-resistance-encoding gene or a gene which complements that missing in an auxotrophic mutant, as described above with reference to the shuttle plasmid. In the auxotrophy strategy, an auxotrophic mycobacterial mutant (e.g., a pyr$^-$F mutant) is isolated and the gene present in the corresponding wild-type (nonmutant) mycobacterium is incorporated into the plasmid. In addition to the pyr$^-$F mutant, it is possible to isolate deoxyglucose mutants, which have a defect in the glucokinase gene, as well as others having mutations in other biosynthetic pathways (e.g., mutations in amino acid biosynthesis, vitamin biosynthesis and carbohydrate metabolism, such as arabinose and galactose).

In either approach, a mycobacterial mutant is selected and the gene which complements the mutation is incorporated into the plasmid vector, which also contains the antigen-encoding DNA of interest. The mycobacterial mutants into which the antigen-encoding DNA is successfully introduced will be identifiable (can be selected) by culturing on appropriately-selected media (e.g., media containing the antibiotic against which resistance is conferred, media containing or lacking the nutrients involved in the biosynthetic pathway affected in the mutant used) or by selecting on the basis of the appearance of plaques formed, when the cI gene is used.

Another component of a plasmid useful in introducing antigen-encoding DNA into the recombinant mycobacteria vaccine vehicle is an autonomously replicating sequence (e.g., a replicon), whose presence is a key determinant in allowing the plasmid to replicate autonomously (extra-chromosomally). These sequences can include, for example, a plasmid replicon, segments of a mycobacteriophage or chromosomal replication origins.

The design of the shuttle plasmid phAE1 includes several of these factors. For example, introduction of the E. coli cosmid pHC79 into the mycobacteriophage TM4 made it possible to provide an E. coli plasmid replicon origin and a selectable ampicillin resistance gene, as well as the bacteriophage lambda cohesive (cos) sequences and a unique EcoRI site. There are no EcoRI sites within the TM4 phage; the unique EcoRI site within phAE1 can be used for introducing foreign gene(s) into the plasmid. As described in Example 4, a 1.6 kb EcoRI fragment encoding the aminoglycoside phosphotransferase (aph) gene from Tn903 has been cloned into phAE1 using this cosmid cloning strategy.

Figure 8:
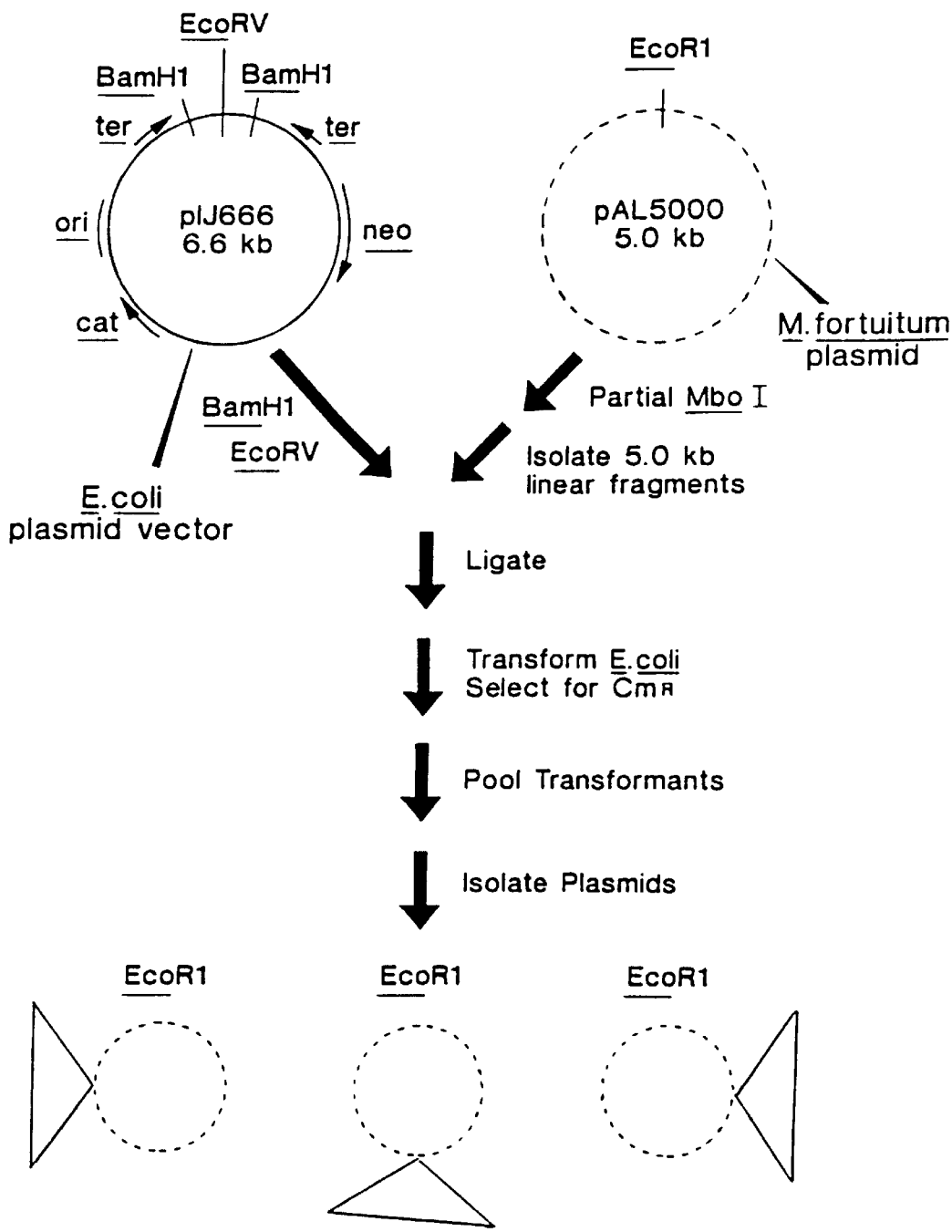
FIG. 8 is a schematic representation of the overall strategy used to generate a library of hybrid plasmid molecules consisting of an *E. coli* plasmid, pIJ666, that contains marker genes conferring resistance to neomycin/kanamycin (neo) and chloramphenicol (cat), inserted at random sites around the pAL5000 genome.

There are several useful approaches to efficiently introduce the antigen-encoding DNA into a cutivable mycobacterium, such as *M. bovis*-BCG or *M. smegmatis*, which is to be used as a vaccine vehicle. For the plasmid, which includes DNA encoding the antigen(s) of interest, a selectable marker and an autonomously replicating sequence, protoplast fusion can be used for efficient introduction into the mycobacterium. In this case, *E. coli* or streptomyces having a cloned plasmid is fused, using known techniques, with a mycobacterial spheroplast. Using this approach, it is possible to transfer the foreign (antigen-encoding) DNA into the mycobacterium. Alternatively, *E. coli* minicells, which contain plasmid DNA and essentially no chromosomal DNA, can be used in carrying out a minicell protoplast fusion.

If, in the alternative, DNA of interest can be moved efficiently into the mycobacterium, an autonomously replicating sequence is not necessary and, instead, the DNA of interest (e.g., antigen-encoding) can be integrated into the mycobacterial chromosomes. This can be accomplished, for example, using minicell protoplast fusion. In this case, a selectable marker for the mycobacterium, which can be an antibiotic-resistance gene or a chromosomal mutation, can be cloned into an *E. coli* cosmid. Also present in the *E. coli* cosmid will be DNA which allows efficient integration of DNA of interest into the mycobacterial chromosome. For example, in *M. leprae*, a repetitive sequence occurs which appears to be associated with recombination; analogous sequences can be identified in and isolated from BCG and *M. smegmatis*, incorporated into the *E. coli* cosmid (along with the selectable marker) and result in a high degree of recombination.

A gene or genes of interest (encoding one or more antigens) can be incorporated into the construct described (e.g., which includes an *E. coli* replicon, a segment of mycobacterial chromosomal DNA associated with recombination (a recombinogenic sequence) and two selectable markers-one serving as a marker in *E. coli* and the second serving as a marker in the mycobacterium). The gene(s) can then be integrated into mycobacterial chromosomal DNA, such as BCG or *M. smegmatis* chromosomal DNA. If the gene(s) of interest are integrated in this way into *M. smegmatis*, it/they can also be moved into BCG by means of a general transducing phage. In this case, it is preferable to include, in addition to the other construct components, two recombinogenic sequences: one from *M. smegmatis* and one from BCG.

Methods of producing and using the recombinant mycobacteria of the present invention are described in detail in the following sections. Those sections describe and exemplify: introduction of DNA of interest into mycrobacteria by means of a shuttle plasmid, to integrate the DNA of interest into mycobacterial chromosomal DNA; introduction of DNA of interest into mycobacteria by means of a shuttle plasmid, to produce mycobacteria in which the DNA of interest is expressed episomally; introduction of DNA of interest into mycobacteria by means of a recombinant plasmid vector, to integrate DNA of interest into mycobacterial chromosomal DNA through homologous recombination; characteristics of the recombinant mycobacteria; and uses of such products.

Introduction of DNA of interest by means of a shuttle plasmid

The present work has resulted in identification of a mycobacteriophage which stably lysogenizes *M. smegmatis*. One such phage, L1, had previously been reported to produce turbid plaques on *M. smegmatis* and putative lysogens were resistant to superinfection and could be induced to produce phage. Doke, S. *J. Kunamoto Med. Soc.* 34, 1360–1373 (960). Tokunaga, T. & Sellers, M. I. in *Host-Virus Relationships in Mycobacterium, Norcardia, and Actinomycetes* (eds. Juhasz, S. E. & Plummer, G.) 227–243 (Charles C. Thomas, Springfield, Ill., 1970). These observations have been confirmed and, in addition, Southern analysis has demonstrated that a prophage is integrated in the *M. smegmatis* chromosome (FIG. 5, Panel B, lanes 2, 3). Analysis of multiple independent lysogens revealed identical patterns of unique bands resulting from the phage integration, which suggests that L1 phage integration is site-specific (FIG. 5, Panel B).

L1 has, thus, been shown to stably lysogenize *M. smegmatis*. L1-shuttle phasmids were constructed by introducing the *E. coli* cosmid, pHC79, containing a ColE1 origin of replication and an ampicillin-resistance gene for selection in *E. coli*, into a non-essential region of the L1-genome (FIG. 6). The L1-shuttle plasmid, designated phAE15, was shown to replicate in *E. coli* as a plasmid and in mycobacteria as a phage and, like the parent phage, integrates into the *M. smegmatis* chromosome (FIG. 5, Panel B, lanes 4, 5). L1 phage is devoid of EcoRI sites. The introduction of pHC79 provided a unique EcoRI site for the pHAE15 shuttle vector, making it possible to introduce genes of interest. It has been shown that these genes can be introduced and stably maintained within the mycobacteria upon lysogenization with the shuttle plasmid vector (FIG. 6).

A 1.6 kb fragment containing the aminoglycoside phosphotransferase (aph) gene from Tn903, which confers kanamycin-resistance in *E. coli*, was introduced into phAE15 by a cosmid cloning strategy. Oka, A., Sugisaki, H. & Takanami, M. *J. Mol. Biol.* 147, 217–226 (1981) The aph gene with EcoRI ends was ligated to linear phAE15 DNA and packaged in vitro into bacteriophage lambda-heads. The resulting recombinant molecules were transduced into *E. coli*. Closed circular plasmid DNA was isolated from an *E. coli* clone that was resistant to both ampicillin and kanamycin, and was transfected into *M. smegmatis* protoplasts. This resulted in mycobacterial phage particles which had packaged plasmid DNA. This plasmid; designated phAE19, has the ability to lysogenize *M. smegmatis* cells and generate kanamycin-resistance colonies (FIG. 7). Mycobacteriophages induced from these lysogens co-transduced immunity to L1 infection and kanamycin-resistance to sensitive *M. smegmatis* cells, demonstrating that the resistance to kanamycin results from expression of the cloned aph gene. phAE19 can also lysogenize and confer kanamycin-resistance upon *M. bovis*-BCG. Kanamycin-resistance thus represents the first useful selectable marker for the mycobacteria. In addition, these results demonstrate that lysogeny is one means by which DNA of interest can be introduced and expressed in mycobacteria.

Introduction of DNA of interest by means of a shuttle plasmid

Introduction of DNA of interest by means of a shuttle plasmid extends the capabilities of phages by offering increased cloning capacity, ease of DNA manipulation, and increased copy number. Plasmids from *M. smegmatis* have not been described previously and genetic manipulation in mycobacteria is difficult. Therefore, a shuttle plasmid vector capable of replicating and expressing DNA of interest in both E. coli and mycobacteria was constructed as follows. In order to ensure a functional replicon for mycobacteria, an E. coli plasmid, pIJ666, containing the neomycin/kanamycin phosphotransferase II (neo) gene from Tn5, and the P15A origin of replication and the chloramphenicol acetyltransferase (cat) gene from pACYC184, was inserted randomly into the plasmid pAL5000, which replicates in M. fortuitum. Kieser, T. and R. E. Melton, Gene, 65:83–91 (1988); Berg, D. E. et al., Proc. Natl. Acad. Sci. U.S.A., 72:3628–3632 (1975); Chang, A. C. Y. and S. N. Cohen, J. Bact., 134:1141–1156 (1978); Labidi, A. et al., FEMS Microbiology Letters, 30:221–225 (1985). FIG. 8 outlines the construction of the pIJ666::pAL5000 library.

Figure 9:
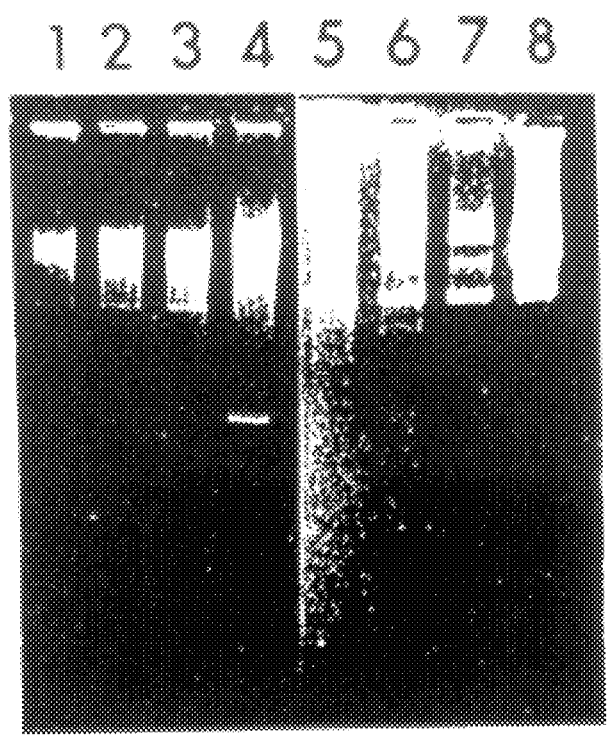
FIG. 9 shows results of agarose gel electrophoretic analysis of DNA from pIJ666::pAL5000 recombinant shuttle plasmids isolated from 3 independent pools of *M. smegmatis* transformants (lanes 1, 2, 3). Following separate transformations of each of these plasmid pools into *E. coli* strain χ2338, unique plasmids were isolated from single purified transformants, designated pYUP13, pYUP14 and pYUP15, and are shown in lanes 5, 6, and 7, respectively. Lane 4 contains the *M. fortuitum* plasmid, pAL5000, and lane 8 contains the library of pIJ666::pAL5000 recombinants. The size of the shuttle plasmids isolated from either *M. smegmatis* or *E. coli* is identical to the size of the recombinant library, indicating stability of the construct.
Figure 10A:
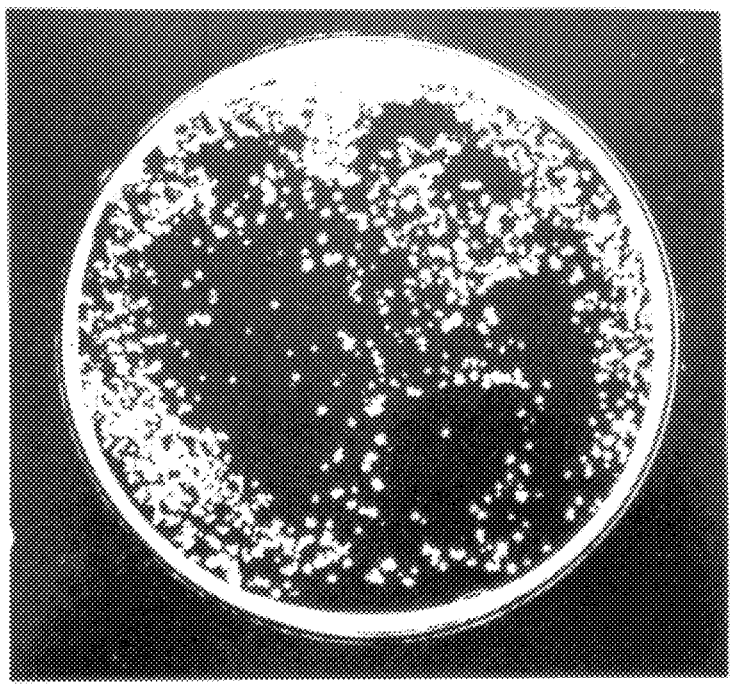
FIGS. 10A & 10B show transformation of BCG with shuttle plasmid DNA. Panel A showns kanamycin-resistant BCG colonies that arose after electroporation of BCG cells with shuttle plasmid DNA; Panel B shows kanamycin-resistant BCG colonies that arose after electroporation of BCG cells without shuttle plasmid DNA.
Figure 10B:
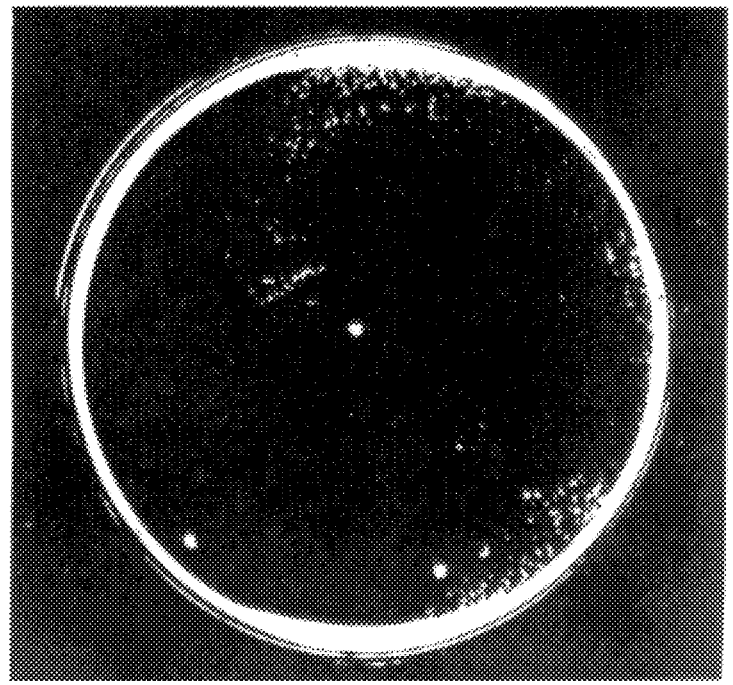

Transformation of this library into M. smegmatis spheroplasts has been difficult, possibly due to the problem of regenerating viable cells. DNA was therefore introduced directly into intact M. smegmatis cells by electroporation to obviate possible damage to mycobacterial cells which might result from use of protocols for producing spheroplasts. Conditions were developed for electroporation of lytic phage DNA that yielded more than $5 \times 10^3$ pfu/ug. Electroporation of the pIJ666::pAL5000 library under these conditions into M. smegmatis yielded kanamycin- and chloramphenicol-resistance transformants. Plasmid DNA isolated from pools of M. smegmatis transformants in three separate experiments was transformed back into E. coli, selecting for kanamycin-resistance. Although pIJ666 was inserted at different sites within the pAL5000 genome in many of the isolated E. coli transformants, all plasmids were stable in both species (FIG. 9). These methods have made it possible to transform some BCG vaccine strains with the pIJ666::pAL5000 recombinant library, with expression of kanamycin-resistance, as described in Example 9 and shown in FIG. 10. Panel A of FIG. 10 shows kanamycin-resistant BCG colonies which arose after electroporation of BCG cells with shuttle plasmid DNA; panel B shows kanamycin-resistant BCG colonies that arose after electroporation without shuttle plasmid DNA. Using a similar approach, the 65 kD M. leprae gene has been introduced into BCG, in which it was expressed, as shown by results presented in FIG. 17.

Figure 11:
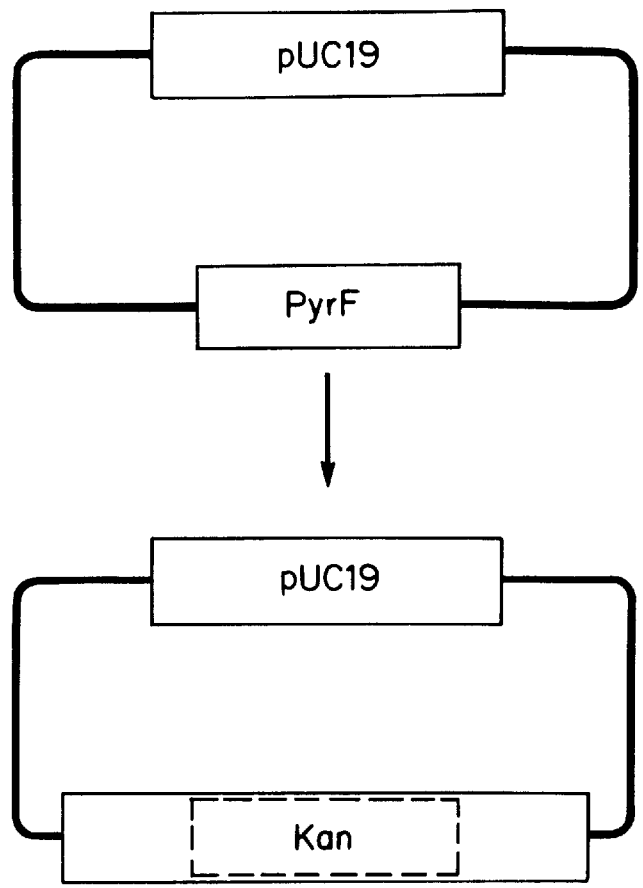
FIG. 11 is a schematic representation of the construction of a recombinant plasmid in which there is a Kan insertion in the PyrF gene of the plasmid vector pUC19.

Plasmid vector for integration of DNA of interest into mycobacterial genomic DNA A plasmid vector, which has been used to integrate DNA of nonmycobacterial origin (i.e., from a source other than the mycobacteria into which it was integrated) in mycobacterial genomic DNA, was constructed as represented in FIG. 11. Isolation of the M. bovis-BCG PyrF gene was carried out as follows and as described in Example 10. M. bovis-BCG DNA was partially digested with a restriction enzyme Sau3A, size selected and inserted into the vector pUC19. The resulting library was used to transform E. coli cells which had an insertion in the E. coli PyrF gene. Four independent colonies which had acquired the ability to grow in the absence of uracil were identified and plasmid DNA was isolated from them. This plasmid DNA was used to construct the recombinant plasmid vector. The PyrF gene of M. smegmatis was incorporated into the pUC19 plasmid vector at the BamHI site and the kanamycin resistance gene (Kan) was inserted into the PyrF gene at the BamHI site, using known techniques. PyrF$^+$ cells are able to grow in medium without uracil and are fluoro-orotic acid sensitive (FOA$^S$); PyrF$^-$ cells need uracil for growth and are fluoro-orotic acid resistant (FOA$^R$). Cells containing the kanamycin resistance gene are kamanycin resistant (KAN$^R$) and those without the gene are kanamycin sensitive (KAN$^S$). Ausubel, F. M. et al. (ed.) Current Protocols in Molecular Biology, p. 1.5.4, Green Pub. (1987). Plasmid DNA containing DNA from pUC19, Mycobacterium smegmatis and Tn903, designated pRH1100, has been deposited, according to the terms of the Budapest Treaty, at the American Type Culture Collection (Rockville, Md.) under accession number 40468 (deposit date Jul. 6, 1988). All restrictions on public access to the deposit will be removed irrevocably upon grant of a United States patent based on this application.

Figure 12A:
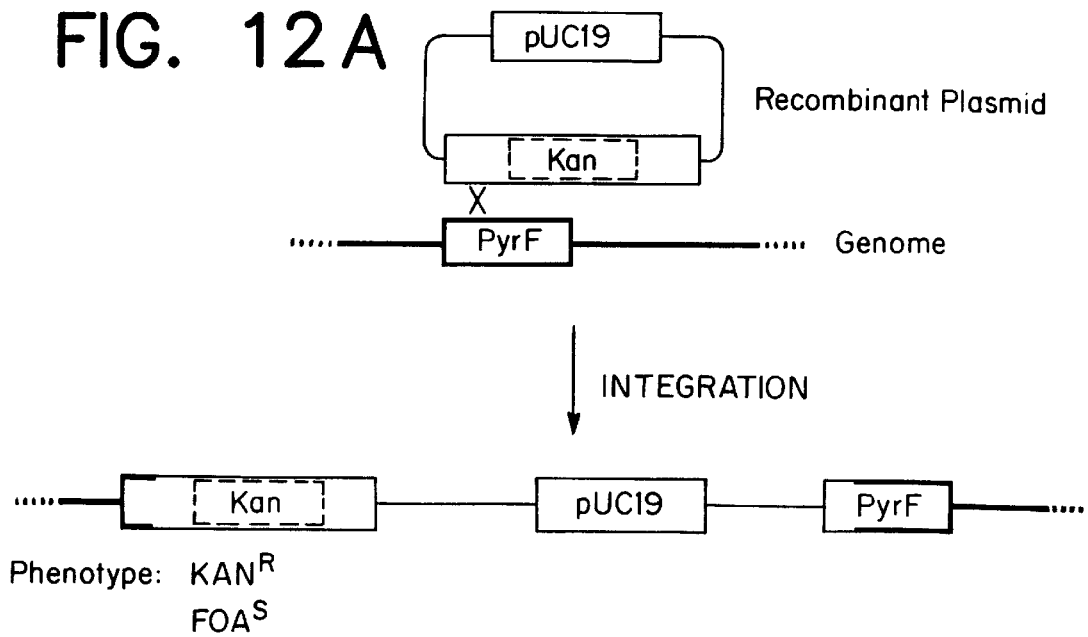
FIGS. 12A and 12B is a schematic representation of transformation of mycobacterial cells with the pUC19 recombinant plasmid in which the PyrF gene contains a Kan insertion.

Stable Integration of DNA of Nonmycobacterial Origin into Mycobacterial Genomic Material As described below and in Example 10, electroporation was used to introduce the resulting recombinant plasmid vector into mycobacteria. As represented in FIG. 12A, in cells transformed with the recombinant plasmid, homologous recombination occurred between sequences on the incoming recombinant plasmid containing the PyrF gene and homologous mycobacterial chromosomal (genomic) sequences, in integration of the incoming PyrF and Kan sequences. Mycobacterial cells containing the integrated recombinant plasmid, which contains the Kan gene, were selected by culturing the electroporated cells on kamanycin-containing medium. Only those cells in which integration of the Kan gene occurred survived.

Figure 12B:
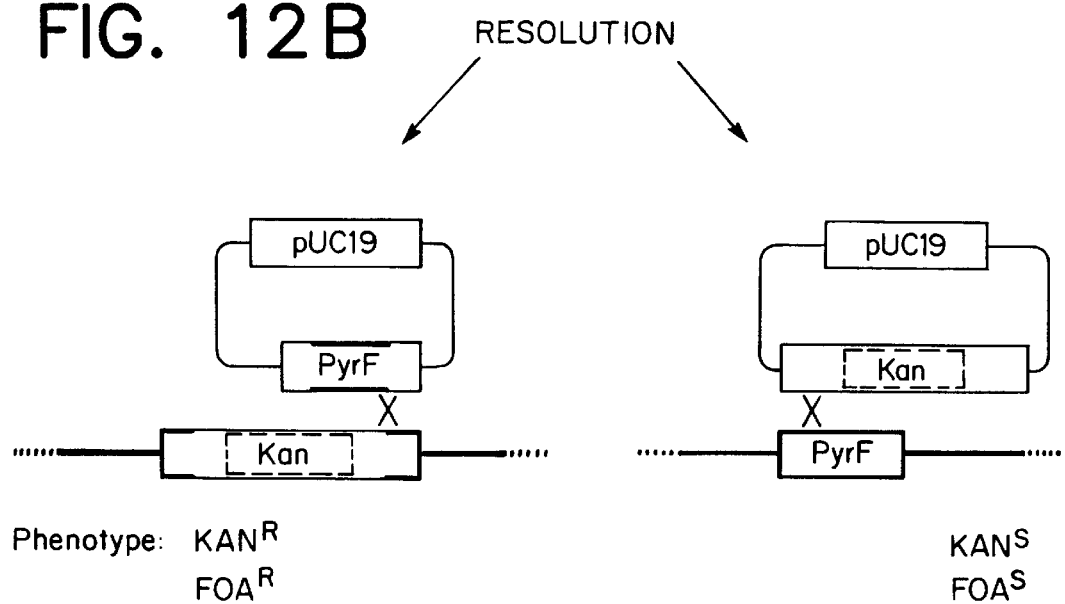

Mycobacterial cells in which the DNA of interest (here, the Kan gene) were identified as follows. The entire integrated recombinant plasmid is unstable because the mycobacterial genome into which it integrates contains two identical sequences in close proximity to one another. As a result, recombination of homologous sequences can again occur. This results in looping out (also called resolution), which results in removal of the recombinant plasmid, producing no net change in the mycobacterial genome, or in removal of the recombinant plasmid in such a manner that the Kan-containing PyrF gene remains in the mycobacterial genome. Resolution occurs with low frequency, but cells in which it has occurred can be identified and isolated on the basis of the phenotype they exhibit. PyrF$^+$ cells (those in which no net change in the genome results), as indicated in FIG. 12, will be kanamycin sensitive and fluoro-orotic acid sensitive (FOA$^S$). Cells in which resolution results in integration of the Kan-containing PyrF gene are kanamycin resistant and exhibit FOA$^R$ because the PyrF gene is disrupted and, thus, nonfunctional. Thus, plating of the KAN$^R$ mycobacterial population on FOA-containing medium will result in identification of cells in which the Kan gene is stably integrated into genomic DNA (FIG. 12B, lower left: KAN$^R$, FOA$^R$).

Thus, the Kan gene was stably integrated into the mycobacterial genome, using homologous recombination of adjacent PyrF sequences. An important advantage of the method of the present invention, which is illustrated in FIG. 12B, is that integration of the DNA of interest occurs without concomitant integration of plasmid or phage DNA into the genome. That is, the net effect is that the plasmid sequences are not present in the recombinant mycobacterial cells. Expression of the Kan gene was also demonstrated and cells in which both integration and resolution had occurred selected for on the basis of cell phenotype (in this case, KAN$^R$, FOA$^R$). In the work described above, DNA of nonmycobacterial origin (i.e., kanamycin resistance gene) was successfully introduced and stably integrated into M. smegmatis genomic DNA. The same techniques can be used to introduce DNA of nonmycobacterial origin into M. bovis-BCG or other mycobacterial genomic DNA.

Stable Integration of DNA Encoding an Antigen or Antigens into Mycobacterial Genomic DNA

Integration of an Interrupted PyrF Gene

Figure 13:
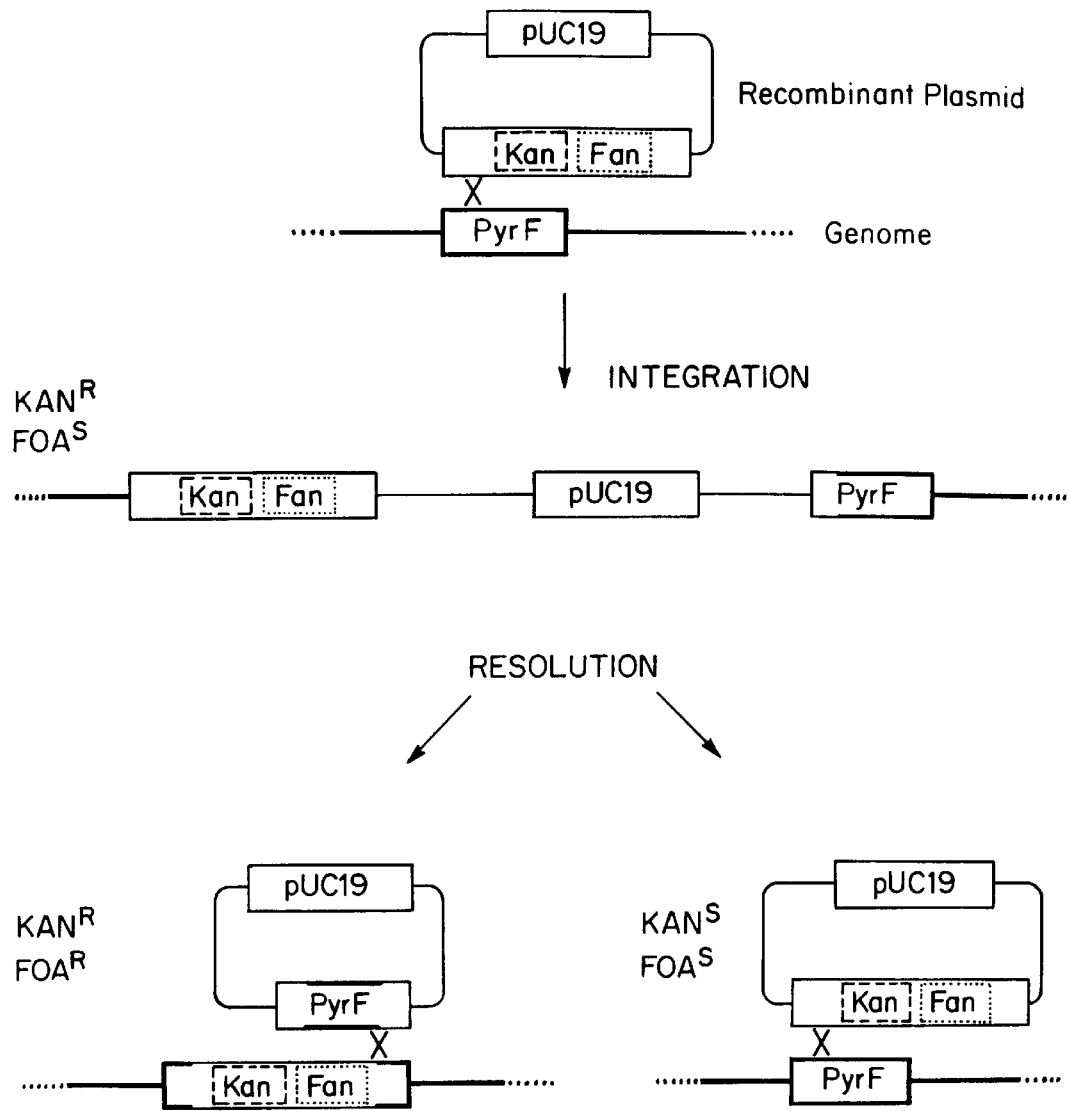
FIG. 13 is a schematic representation of the integration of Kan and DNA encoding a selected antigen (designated Fan) into mycobacterial DNA.

In a similar manner, DNA encoding one or more antigens against which an immune response is desired can be integrated into mycobacterial genomic DNA. The method of the present invention, by which DNA of interest is integrated into mycobacterial genomic DNA, is represented schematically in FIG. 13. The method will be described with particular reference to integration of DNA which is the 65 KD *M. leprae* gene into *M. smegmatis*, which has been carried out (see Example 11). It is to be understood, however, that the same approach can be used to introduce the *M. leprae* 65 KD gene into other mycobacteria, as well as to integrate DNA encoding other polypeptides or proteins against which an immune response is sought into *M. bovis*-BCG, *M. smegmatis* or other mycobacteria.

Integration of DNA encoding a selected antigen (designated Fan, for foreign antigen) is represented in FIG. 13. An appropriate plasmid vector (e.g., one which can replicate in *E. coli* but not in mycobacteria), such as the recombinant pUC19 plasmid represented in FIG. 13, is used. The recombinant plasmid includes a mycobacterial gene or DNA sequences such as the PyrF gene represented in FIG. 13; sequences in this gene, which are homologous to those in the mycobacterial genome, provide the basis for homologous recombination between plasmid-borne mycobacterial sequences and genomic mycobacterial sequences to occur. The recombinant plasmid also includes DNA sequences necessary for replication and selection in *E. coli* and DNA sequences necessary for selection in mycobacteria. The sequences for use in selection confer a distinctive phenotype on the cell, thus making it possible to identify and isolate cells containing the gene. The gene can encode, for example, drug resistance. In FIG. 13, the recombinant plasmid includes a gene conferring kanamycin resistance, thus making it possible to select mycobacteria containing the gene simply by culturing on kanamycin-containing medium. The recombinant plasmid also contains DNA encoding one or more polypeptide or protein against which an immune response is desired (designated Fan), which is integrated into mycobacterial genomic DNA.

In one embodiment of the present invention, the 65 KD gene of *M. leprae* has been integrated into *M. smegmatis* genomic DNA through use of a recombinant plasmid as represented in FIG. 13, in which Fan is the *M. leprae* gene.

The recombinant plasmid (e.g., a plasmid containing the PyrF gene into which the 65 KD *M. leprae* gene and a Kan gene were inserted) was introduced into mycobacterial cells (*M. smegmatis*) using standard electroporation techniques. (See Example 11). Electroporated cells were then plated onto kanamycin-containing medium. Only kanamycin-resistant ($KAN^R$) cells grew under these conditions; such cells had integrated into genomic DNA the $KAN^R$ gene and the *M. leprae* gene and were also $FOA^S$ (due to the disrupted PyrF genes from the recombinant plasmid and from the mycobacterium).

Cells were subsequently transferred to FOA-containing medium to identify those cells in which the Fan gene (here, the *M. leprae* gene) was stably integrated into genomic DNA. As indicated in the bottom panel of FIG. 13 (left side), integrated into genomic DNA of such cells ($KAN^R$, $FOA^R$) is the disrupted PyrF gene which contains the kanamycin resistance gene and the Fan gene. As indicated at the right side of the bottom panel, mycobacterial cells which have undergone looping out with the result that only a complete PyrF gene remains in the genome are both kanamycin sensitive and fluoro-orotic acid sensitive.

Thus, as described above and in Example 11, it has been possible to integrate into mycobacterial genomic DNA DNA encoding a protein antigen and to identify and select those cells which contain the stably integrated DNA of interest. In addition, such DNA of interest has been integrated into the mycobacterial genome at a selected site (in this case, at the PyrF gene site). This same approach can, of course, be used to integrate DNA of interest into other selected sites on mycobacterial genomic DNA. In this case, a site on the genome, at which integration is desired, can be selected. A recombinant plasmid containing sequences homologous to or sufficiently similar to the selected genomic sequences; DNA of interest; sequences necessary for replication and selection in *E. coli*; and DNA sequences necessary for selection in mycobacteria can be constructed, as described previously. The DNA of interest can be stably integrated into mycobacterial genomic DNA and cells containing the stably integrated DNA of interest selected, in the same manner as described previously.

It is possible to introduce all or a portion of any gene whose expression in mycobacteria is sought into mycobacteria using the same method. That is, the following method can be used to stably integrate into a mycobacterial genome DNA of interest:

A recombinant plasmid vector, which can replicate in *E. coli* but not in mycobacteria and which includes:

1. a mycobacterial gene, or portions thereof, necessary for recombination with homologous sequences in the genome of mycobacteria transformed with the recombinant plasmid;
2. all or a portion of a gene which encodes a polypeptide or protein whose expression is desired in mycobacteria transformed with the recombinant plasmid;
3. DNA sequences necessary for replication and selection in *E. coli*; and
4. DNA sequences necessary for selection in mycobacteria (e.g., drug resistance).

is used to transform mycobacterial cells, such as *M. smegmatis* or *M. bovis*-BCG. The recombinant plasmid is introduced into mycobacterial cells using known techniques. In one embodiment, the plasmid is introduced by means of electroporation, using standard bacterial electroporation procedures. (See Example 11).

Electroporated cells are plated under conditions which allow selection of cells in which integration has occurred. As described above, the plasmid can contain a gene encoding drug resistance; such as kanamycin resistance. In that instance, electroporated cells are plated onto medium containing kanamycin. Only kanamycin resistant ($KAN^R$) cells, which are cells in which plasmid DNA has been integrated, will survive under these conditions.

Surviving cells are subsequently plated under conditions which make it possible to identify and select those in which the DNA of interest is stably integrated in genomic DNA. In the case in which the PyrF gene has been disrupted by insertion of DNA of interest, surviving cells are plated onto FOA-containing medium, which makes it possible to identify cells in which resolution has occurred because they are $FOA^R$ (and, thus, grow in such medium).

The DNA encoding a polypeptide or protein against which an immune response is sought, which is present in the recombinant plasmid, can be isolated from a source in which it occurs in nature, produced by means of standard genetic engineering techniques, in an appropriate host, or synthesized chemically or mechanically. Similarly, plasmid-borne DNA sequences necessary for homologous recombination can be isolated from a source in which it occurs in nature, produced by means of standard genetic engineering techniques or synthesized chemically or mechanically. The characteristic which serves as the basis for selection of mycobacterial cells containing integrated DNA of interest can be, as described, drug resistance. The gene can encode, for example, kanamycin resistance, viomycin resistance, thiostrepton resistance, hygromycin resistance or bleomycin resistance. Alternatively, an auxotrophy strategy can be used, such that selection is based on the ability of mycobacteria in which integration has occurred to survive, when grown on appropriate medium.

Integration of a PyrF-DNA of Interest (Fan) Combination

Figure 14:
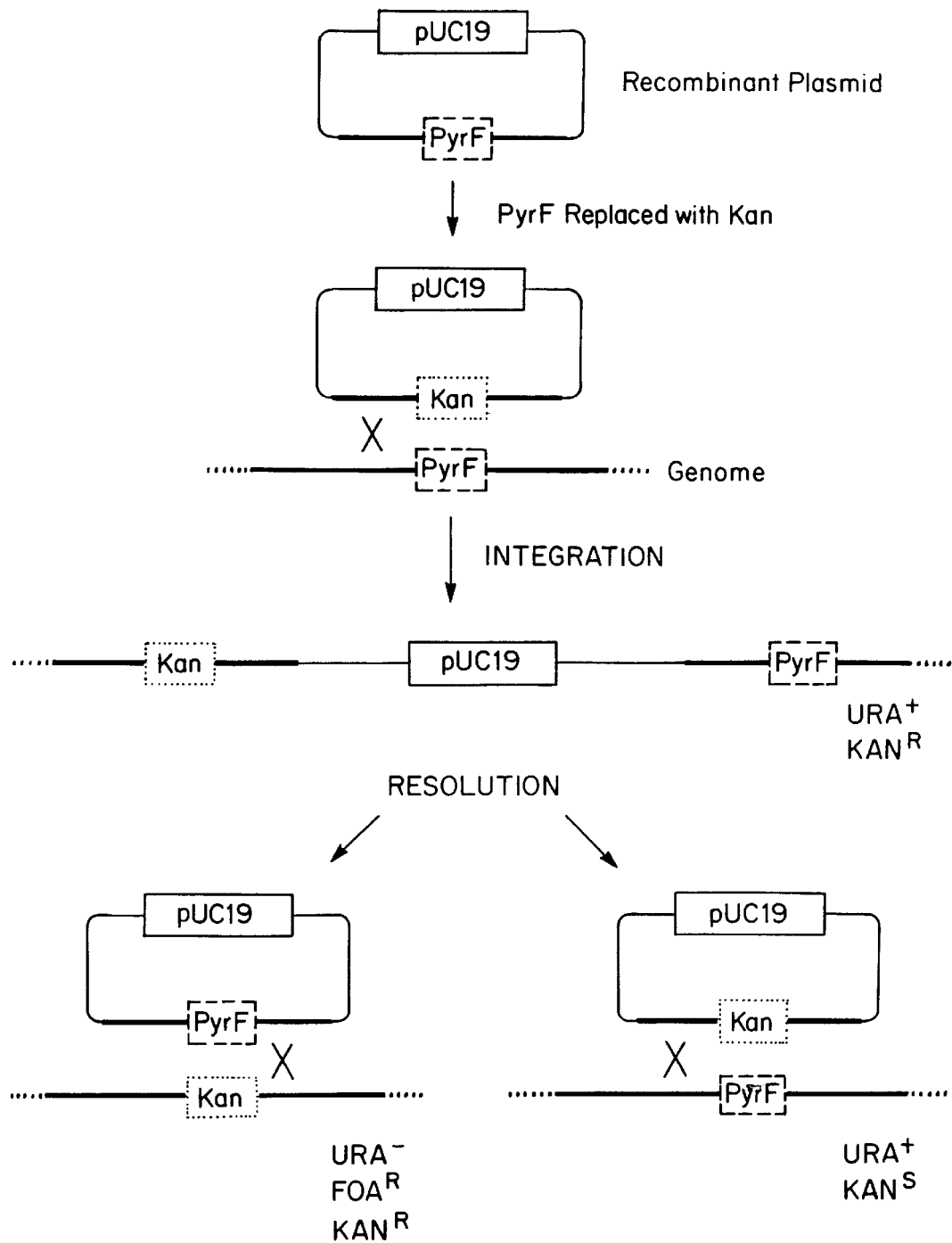
FIG. 14 is a schematic representation of replacement of the mycobacterial PyrF gene with a gene encoding kanamycin resistance.

An alternative approach to that described above, in which a mycobacterial gene (e.g., PyrF) is disrupted by a drug resistance gene and DNA of interest, is one in which DNA of interest is integrated into a mycobacterial genome without additional sequences (e.g., without the Kan gene), as occurs as a result of the earlier described method. This method is represented in FIG. 14.

In this method, recombinant mycobacterial cells which are targets for further manipulation and introduction of DNA of interest are first produced. This can be done, for example, by making a precise replacement of the mycobacterial PyrF gene by a kanamycin resistance gene. Standard recombinant DNA techniques are used in this replacement procedure, in which sequences flanking the PyrF gene are used to insert the Kan gene. The recombinant plasmid (in which the PyrF gene is replaced with Kan) is introduced into mycobacterial cells using standard electroporation methods. The resulting electroporated cells are plated onto medium containing kanamycin and no uracil. Mycobacterial cells in which both the kanamycin resistance gene and the genomic PyrF gene are present will be selected at this point. All other cells ($KAN^R Ura^-$; $KAN^S Ura^-$; $KAN^S Ura^+$) will die. Cells selected in this manner are subsequently plated onto medium containing kanamycin, fluoro-orotic acid and uracil. As shown in FIG. 14, this results in selection of mycobacterial cells which are $URA^-$ and $FOA^R$ (because they contain no PyrF gene), as well as $KAN^R$ (because of the integrated Kan gene).

Figure 15:
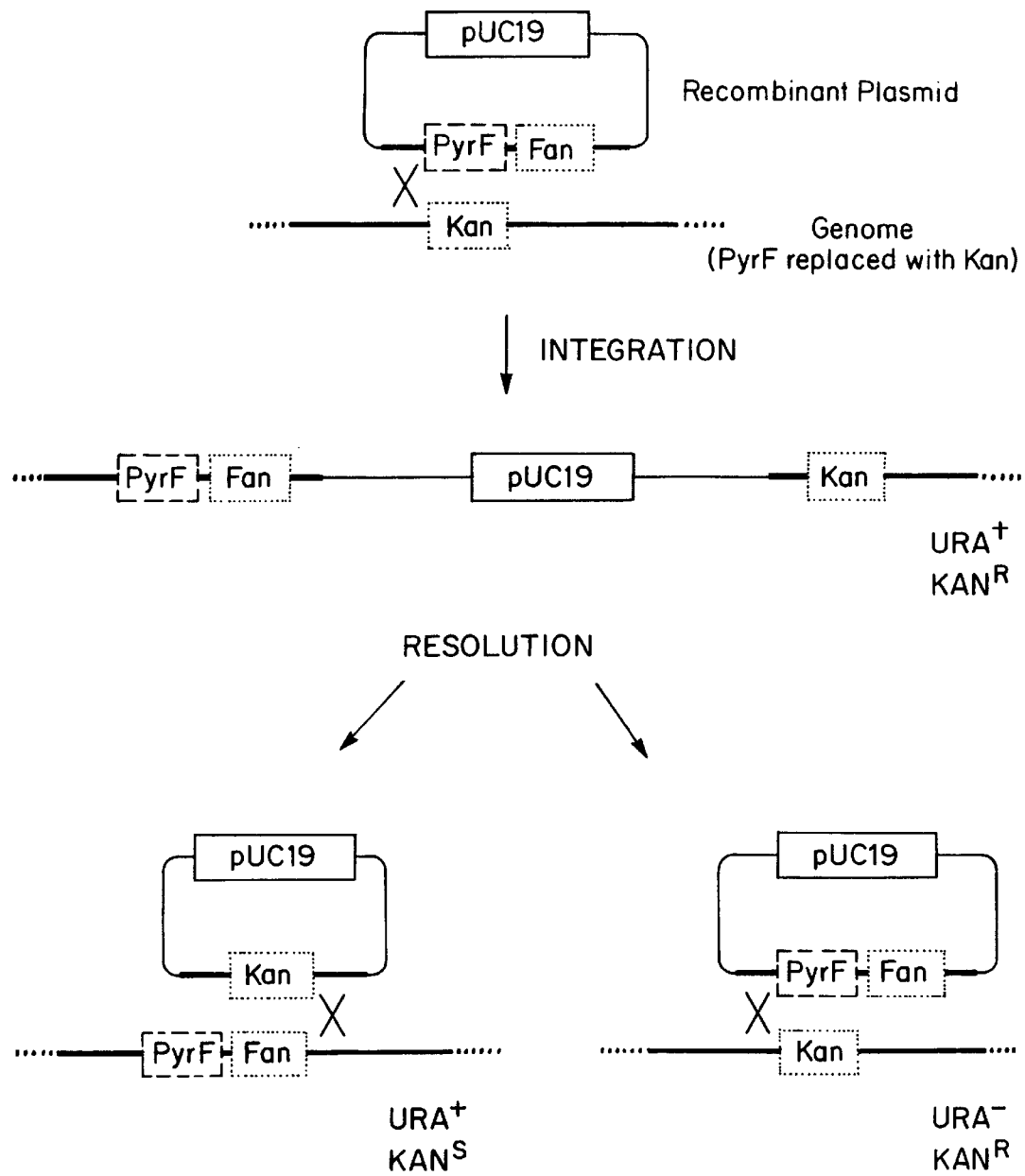
FIG. 15 is a schematic representation of integration of a PyrF gene and DNA of interest into a recombinant mycobacterium produced as represented in FIG. 14.

Mycobacterial cells produced in this manner are used in this method as targets (target mycobacterial cells) for further manipulation, using known techniques, by which DNA of interest, and an intact PyrF gene are integrated into mycobacterial genomic DNA. As represented in FIG. 15, a recombinant plasmid, similar to that described previously and in Example 10, which includes an intact PyrF gene and DNA of interest (next to or closely following one end of the PyrF gene) is used. The recombinant plasmid is introduced into the "target" mycobacterial cells (which include a Kan gene and no PyrF gene) using standard techniques (e.g., electroporation). Homologous recombination occurs between sequences to one side of the Kan gene present in the target mycobacterial cells and to one side of the PyrF gene present in the recombinant plasmid, resulting in integration into the target mycobacterial cells genomes of the PyrF gene-DNA of interest combinations, as represented in FIG. 15.

Electroporated cells are plated onto medium containing kanamycin and no uracil. Only those cells which contain the kan gene and the PyrF gene (with which the DNA of interest has entered the cells) will survive under these conditions. Subsequent culturing of survivors on medium containing no added uracil will result in growth of only those mycobacteria having integrated into their genomes the PyrF gene-DNA of interest combination, as represented in FIG. 15.

Figure 16:
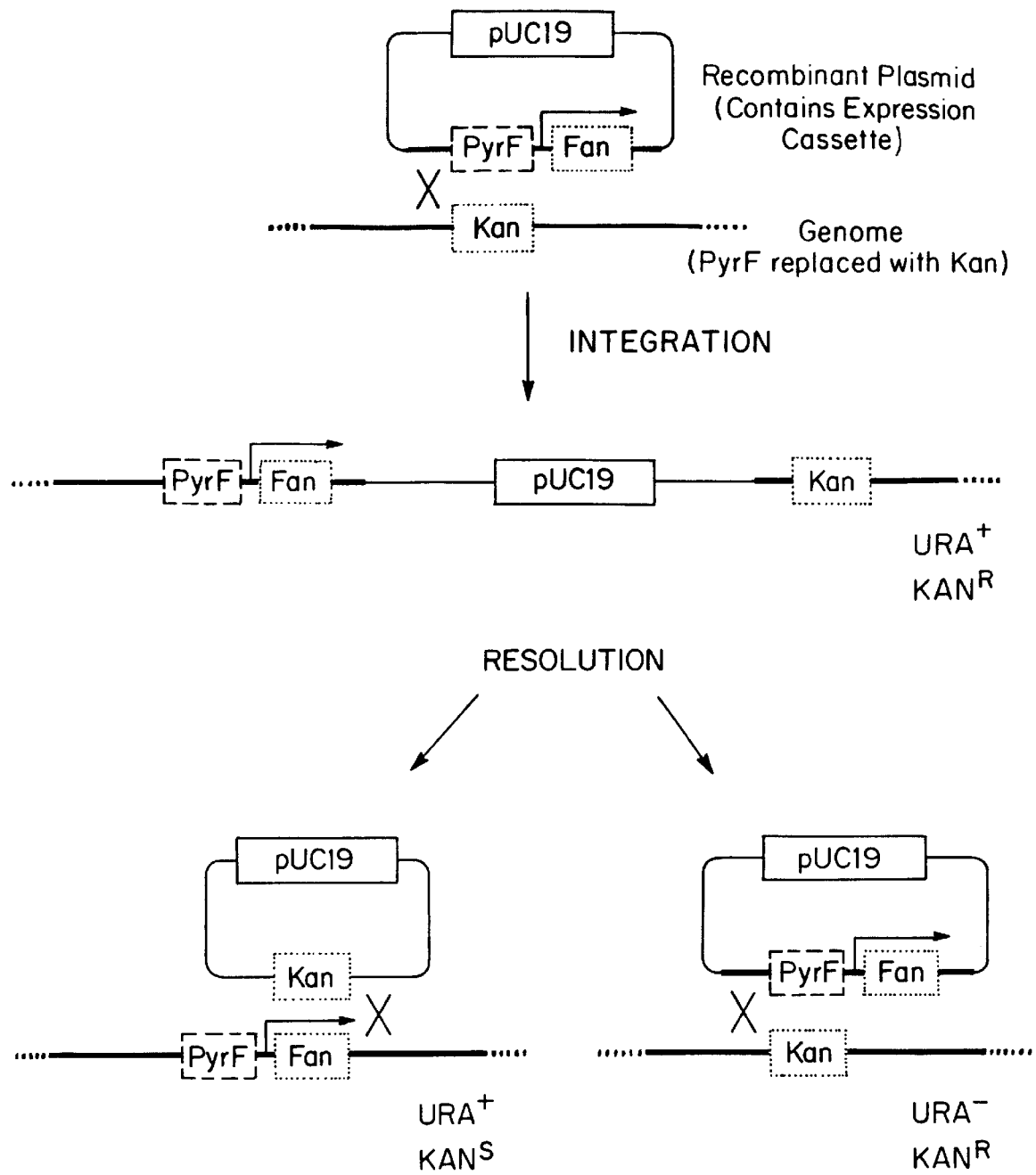
FIG. 16 is a schematic representation of the use of an expression cassette to control expression of DNA of interest integrated into a mycobacterial genome.

In those cases in which DNA of interest is from a source which results in its inability to be expressed in mycobacteria, an expression cassette can be used. The expression cassette can contain a mycobacterial promoter and ribosome binding site, which will serve as expression signals controlling expression of the DNA of interest. As represented in FIG. 16, the expression cassette can include a polylinker in sequences surrounding the pyrF gene. As a result, DNA of interest can be inserted and the mycobacterial signals will control its expression. Selection of mycobacterial cells in which the PyrF-expression cassette-DNA of interest combination are stably integrated can be carried out as described previously in relation to FIG. 15.

A slightly different, but related method by which DNA of interest can be integrated into mycobacterial genomes makes use of mycobacteria from which the normally present PyrF coding sequences normally present have been removed, using known techniques. A recombinant plasmid similar to that described previously except that it includes an intact (undisrupted) PyrF gene in combination with DNA of interest (located at or near one end of PyrF), is introduced into PyrF-deleted mycobacteria (e.g., by electroporation). Cells which contain an intact PyrF gene (and, thus, DNA of interest) are identified by culturing electroporated cells on medium containing no uracil. Only cells containing the PyrF gene will survive. Subsequent growth on medium containing no uracil will also identify those cells in which looping out has resulted in stable integration of PyrF and the DNA of interest into the mycobacterial genome.

The outcome of both of these latter two approaches, in which PyrF is replaced with a Kan gene in or PyrF is deleted from the mycobacterial genome is that the resulting recombinant mycobacterial genome includes a functional PyrF gene and the DNA of interest, but does not contain a gene encoding drug resistance (e.g., Kan) or other selectable marker.

Overview of uses and advantages of shuttle vectors and methods of the present invention There are numerous uses for and advantages of the plasmid and the plasmid vectors of the present invention, as well as for the method of the present invention in which they are used. These are described below and their use in constructing vaccine vehicles is described in the following sections. As a result of the present invention, by which DNA introduced into mycobacteria has been expressed, new genetic approaches to understanding questions of disease pathogenesis are now available. Using either phage or plasmid vector systems, it should be possible to insertionally mutagenize and mark genes of pathogenic mycobacteria, either by homologous recombination or by transposon mediated insertion or deletion, with the aim of identifying specific genetic functions required for virulence and pathogenesis. For example, using these vectors and mycobacteria (e.g., M. smegmatis, M. bovis-BCG), virulence genes of M. tuberculosis or M. leprae can be identified and diagnostics (diagnostic tests) developed. By specifically deleting or replacing those genes, it may be possible to develop a more specific and effective attenuated vaccine against tuberculosis than the current M. bovis-BCG vaccine. Alternatively, as specific protective antigens for tuberculosis and leprosy are identified by study of antigens recognized by T cells from resistant individuals, it will now be possible to introduce and express them in currently existing M. bovis-BCG vaccines.

The vectors of the present invention are the first to make it possible to construct genomic libraries in a mycobacterium. This is particularly useful in identifying antigens or enzymes or drug targets for a pathogenic mycobacterium. For example, in the case of M. leprae, genomic DNA is sheared and cloned, to ensure that the entire genomic DNA is included. Using the subject vectors, the library of the *M. leprae* fragments is first introduced into a bacterial host, such as *E. coli*, where it is expressed. It is subsequently moved into a mycobacterium (e.g., *M. smegmatis*, BCG). As a result, the library exists in a mycobacterial host, thus making it more efficient to look for mycobacterial antigens, enzymes, drug targets and diagnostic probes.

A shotgun approach can be used to introduce DNA into BCG and to identify clones containing genes which enable them to grow faster than presently-available BCG, which is a slow-growing mycobacterium. Genes identified in this manner can subsequently be used to produce BCG which grows faster than presently-used BCG. A similar approach can be used to clone *M. leprae* genes into a cultivable mycobacterium and to identify those recombinant cells which grow. This approach can be used to make *M. leprae* from a cultivable mycobacterium, thus alleviating the present difficulty of producing the pathogen.

The vectors of the present invention can also be used to identify new drugs for the prevention or treatment of tuberculosis or leprosy. For example, it is possible that a target against which a drug should be directed is an enzyme (e.g., gyrase) produced by the causative mycobacterium. The corresponding enzyme-encoding genes in *M. smegmatis* can be replaced, using the subject vectors, with the *M. tuberculosis* or the *M. leprae* enzyme-encoding gene(s). This results in production of a recombinant *M. smegmatis* which can be used for testing to identify drugs effective against the enzymes (as well as for drugs effective against *M. avium* and *M. intracellulare*).

The genetic approaches described herein have made it clear that both the aph and neo genes encoding kanamycin resistance can be (and have been) stably expressed in *M. bovis*-BCG vaccine strains.

As a result of the work described herein, selectable markers (genes encoding identifiable characteristics on which selection can be based) are now available for mycobacteria. Three such selectable markers are now available for mycobacteria: 1) the chloramphenicol acetyl transferase or cat gene, which confers chloramphenicol resistance; 2) the aminoglycoside phosphotransferase or aph gene from Tn903, which confers kanamycin resistance; and 3) the cI gene, which encodes the repressor protein of the L1 bacteriophage. Growth on medium containing the appropriate drug is used in the cases of the drug resistance genes to select mycobacteria containing the cat or the aph gene. Selection of variants on the basis of the appearance (cloudy or clear) of the plaques they form when cultured is used in the case in which the cI gene is used for selection.

Also as a result of the work described herein, lysogeny and site specific recombination have been shown to occur between specific sites, known as attachment, or att sites, on the mycobacterial chromosomal DNA and on the mycobacterial phage. In bacteria infected with phage lambda, the physical condition of the phage DNA is different in the lytic and lysogenic states. Change from one of these states to the other involves site-specific recombination. Integration of lambda DNA into host DNA (resulting in the free lambda DNA's becoming prophage DNA) must occur for lysogeny to occur; conversely, excision of prophage DNA from the host chromosome must occur for lysis to occur. Integration and excision involve site-specific recombination. Although this phenomenon is known for several genera of bacteria, this is the first time it has been demonstrated for mycobacteria. It can be used as a means by which DNA of interest can be incorporated into mycobacteria efficiently and stably.

For example, this can be accomplished by use of what is referred to as a cos-att vector. Such a vector can include: 1) an *E. coli* or other appropriate bacterial origin of replication; 2) a gene encoding a selectable marker, such as ampicillin resistance, for selection in *E. coli* or other bacterial host; 3) the att region of a temperate phage, such as L1; 4) the lambda cos site, in order that lambda in vitro packaging systems can be used; and 5) a gene encoding a selectable marker, such as kanamycin resistance, chloramphenicol resistance or the gene encoding the cI repressor of the phage L1. This vector can be constructed using known techniques and those described herein. Present on the same vector or, alternatively, provided in trans can be genes necessary to mediate integration of the vector.

The work described herein has resulted in identification of plasmid replicons which replicate extrachromosomally in mycobacteria (e.g., *M. smegmatis*, BCG). As described, the pAL5000 replicon has been identified. The same method can be used to identify others which can also be used.

The work described also demonstrates successful construction of *E. coli* mycobacterial shuttle phasmids that are recombinant DNA molecules that not only have the ability to replicate in *E. coli* as plasmids and in mycobacteria as a phages, but also have the ability to be packaged into bacteriophage lambda heads or into mycobacteriophage particles. It further demonstrates that recombinant DNA has been introduced into both a fast-growing mycobacterium (*M. smegmatis*) and a slow-growing mycobacterium (BCG). This makes it possible to infect *M. bovis*-BCG vaccine strains with the shuttle phasmids and, thus, to introduce cloned genes into mycobacteria. Thus, this eliminates the need to develop a transfection system for BCG. That is, because the *E. coli*-mycobacterial shuttle plasmid, upon transfection into mycobacteria, is packaged into mycobacterial particles, DNA of interest can be introduced stably into slow-growing mycobacteria (e.g., *M. bovis*-BCG) by transduction, rather than transfection. This makes it possible to produce recombinant mycobacterial vaccine vehicles, which can be used to immunize against one or more antigens of interest.

The use of in vitro packaging to construct these phasmids can be extended as an efficient strategy for cloning of genes (e.g., genes or DNA of interest encoding an antigen or antigens for one or more pathogens against which an immune response is desired) into these vectors, as long as the size limits of the packaging system are not exceeded. It is also possible, by screening additional L1::pHC79 recombinant phasmids, to determine the maximum amount of DNA that can be deleted from the L1 phage and to define additional non-essential regions of the phage genome into which DNA can be inserted.

Construction of Genetically Recombinant Mycobacteria Useful to Express DNA of Interest The method of the present invention is useful to construct a genetically recombinant mycobacterial vehicle for the expression of the protein(s) or polypeptide(s) encoded by DNA of interest incorporated into the mycobacterium. Such genetically recombinant mycobacteria have many uses.

Vehicles of the present invention can be used, for example, as vaccines to induce immunity against the pathogenic antigen encoded by the DNA of interest. A pathogen is any virus, microorganism, or other organism or substance (e.g., toxins) which causes disease. A vaccine vehicle useful for immunizing against leprosy can be made. Because of the extraordinary adjuvant activity of mycobacteria, such as BCG, such a vaccine would be effective in producing cell-mediated immunity, particularly of a long-term or enduring nature. Genes encoding protein antigens of the leprosy parasite *M. leprae* have been isolated by Young and are described in detail in co-pending U.S. patent application Ser. No. 892,095, filed Jul. 31, 1986, the teachings of which are incorporated herein by reference. In particular, genes encoding five immunogenic protein antigens (i.e., antigens of molecular weight 65 kD, 36 kD, 28 kD, 18 kD and 12 kD) have been isolated. In addition, 6 different epitopes encoded by the gene for the 65 kD antigen have been defined. At least one of these epitopes has been shown to be unique to *M. leprae*; the other epitopes have been shown to be shared with the 65 kD proteins of other mycobacteria.

Through use of the shuttle vectors and recombinant plasmid vectors of the present invention, it is possible to introduce into BCG one or more of the genes encoding *M. leprae* protein antigens, using methods described above and in the following examples. The gene encoding the 65 kD *M. leprae* protein has, in fact, been introduced into and expressed by recombinant BCG. Results of Western blot analysis (FIG. 17) demonstrated the presence of both the 65 kD *M. leprae* antigen and the selectable marker. For example, the gene encoding the 65 kD *M. leprae* antigen can be introduced into BCG, stably integrated into its genomic DNA and expressed at levels sufficient to stimulate or induce an immune response in a host to which it is administered. As described in detail in Example 11, monoclonal antibodies specific for the 65 kD *M. leprae* protein have been used to demonstrate expression of the 65 kD *M. leprae* gene in extracts of *M. smegmatis* into which the gene was introduced. In addition, the gene encoding the SIV1 envelope protein has been cloned into a similar plasmid vector, to be introduced into *M. smegmatis* using the techniques described for the Kan and *M. leprae* genes. A similar construct, for introduction into BCG, has also been made. In this way, it is possible to construct a vaccine which is close to ideal, in that it contains one or more protective antigens of *M. leprae*, does not have tolerogenic determinants and has an excellent adjuvant for inducing cell-mediated immunity.

In a similar fashion, it is possible to construct a vaccine, using a shuttle or plasmid vector and the method of the present invention, to provide specific protection against tuberculosis. Such a vaccine is particularly attractive because of the recently reported finding, described above, that presently-used vaccines are proving to be ineffective. Genes encoding immunogenic protein antigens of the tubercle bacillus *M. tuberculosis* have been isolated and are described in co-pending U.S. patent application Ser. No. 07/010,007, entitled "Genes Encoding Protein Antigens of Mycobacterium Tuberculosis and Uses Therefor", by Robert N. Husson and Richard A. Young, filed Feb. 2, 1987 (now abandoned), and in the continuation-in-part application, Ser. No. 07/154.331, filed by the Express Mail procedure Feb. 10, 1988), entitled "Genes Encoding Protein Antigens of Mycobacterium Tuberculosis and Uses Therefor", by Robert N. Husson, Richard A. Young and Thomas M. Shinnick, the teachings of which are incorporated herein by reference.

In this case, a gene encoding an immunogenic protein antigen of *M. tuberculosis* is introduced into BCG by means of a shuttle or plasmid vector, as described above. It is also possible to introduce more than one *M. tuberculosis* gene, each encoding a protein antigen, into. BCG. For example, a gene encoding immunogenic *M. tuberculosis* antigens of molecular weight 12 kD, 14 kD, 19 kD, 65 kD and 71 kD, or a combination of two or more of these genes, can be inserted into BCG, stably integrated into genomic DNA and expressed. The result is a vaccine which is specific for immunization against tuberculosis and which induces long-lived immunity against the bacillus.

It is also possible, using the method of the present invention, to construct a multipurpose or multifunctional vaccine (i.e., a single vaccine vehicle which contains and expresses DNA of interest which includes more than one gene, each gene encoding a protein antigen for a different pathogen or toxin). For example, it is possible to introduce into BCG, using the shuttle vector plasmid or the plasmid vector described, a gene encoding a protein antigen for *M. leprae*, a gene encoding a protein antigen for *M. tuberculosis*, a gene encoding a protein antigen for Leishmania, and a gene encoding a protein antigen for malaria. Administration of this multi-valent vaccine would result in stimulation of an immune response to each antigen and provide long-term protection against leprosy, tuberculosis, leishmaniasis, and malaria.

The recombinant mycobacteria can also be used as an anti-fertility "vaccine" vehicle. For example, mycobacteria containing DNA encoding antigens such as human gonadotropic hormone (HGH) fragments can be used as an anti-fertility vaccine and administered as a birth control agent. Vaccine vehicles of the present invention can be used to treat human cancers, such as bladder cancers or melanomas (e.g., by expressing growth inhibitors or cytocidal products). In this context, recombinant mycobacteria which contain and express interferon α, β and/or γ, one or more interleukin (interleukins 1–7) and/or TNF α or β are particularly useful. In another application, recombinant mycobacteria can be used to express stress proteins, either for the purpose of eliciting a protective immune response (e.g., against subsequent or long-term infection) or for the purpose of inducing tolerance in an autoimmune disease (e.g., rheumatoid arthritis). Stress proteins, such as those described in co-pending U.S. patent application Ser. No. 207,298, entitled Stress Proteins and Uses Therefore, by Richard A. Young and Douglas Young, filed Jun. 15, 1988, can be used in this purpose. Because of their large genomes (e.g., the BCG genome is about $3\times10^6$ bp long), mycobacteria can accommodate large amounts of DNA of interest and, thus, can serve as multi-purpose vehicles.

Recombinant mycobacteria of the present invention can be used to produce polypeptide(s) of interest, such as steroids. In this case, all or a portion of a steroid-encoding gene is introduced into an appropriate mycobacterial host, in which it is expressed. Thus, the recombinant mycobacteria provide a valuable means of producing such proteins.

In addition, the shuttle vectors and genetically recombinant mycobacteria of the present invention can be used in a diagnostic context. For example, a shuttle plasmid which is specific for (capable of introducing DNA into) a pathogenic organism (e.g., *M. tuberculosis, M. avium*) and includes DNA encoding a reporter molecule (e.g., luciferase from a Vibrio bacterium or of firefly origin; β-galactosidase; β-glucoronidase; catechol dehydrogenase) and a strong mycobacterial promoter (the DNA sequence necessary for initiating transcription), which controls (drives) expression of the reporter molecule-encoding gene, is constructed. A sample (e.g., blood, urine) is obtained from an individual to be assessed for presence or absence of the pathogenic organism. If, for example, the individual is being tested for tuberculosis, a shuttle plasmid specific for *M. tuberculosis* is used. The sample is cultured and combined with an appropriate quantity of the *M. tuberculosis*-specific plasmid. After a short time (e.g., several hours) under appropriate conditions, the sample is assayed, using known techniques, for the occurrence (presence or absence or if desired, the quantity, of the reporter molecule encoded by the DNA in the vector. If the sample contains *M. tuberculosis*, even at very low levels, the DNA present in the phage will be introduced into the organism. Once in *M. tuberculosis* present in the sample, the plasmid (phage) DNA, including that encoding the reporter molecule, will be replicated. If the reporter molecule is luciferase, a considerable quantity of luciferase will be produced (because production is driven by a strong promoter) and can be detected using standard equipment, such as a photometer. Determination of presence or absence of *M. tuberculosis* infection in the individual is thus possible, as is quantitation, if desired. Until the present method was developed, available techniques of diagnosing tuberculosis were slow (e.g., required several weeks). β-galactosidase, which has now been expressed in mycobacteria, can also be used as a reporter molecule.

In any of the uses of the recombinant mycobacteria to express a protein or polypeptide, it is possible to include in the shuttle vector DNA encoding a signal sequence and, thus, provide a means by which the expressed protein or polypeptide is made in the cytoplasm and then secreted at the cell walls. For example, the signal sequence from a antigen, which is secreted in mycobacteria, could be used. Alternatively, the signal sequence for β-galactosidase., agarase or a amylase could be used.

The present invention will now be illustrated by the following examples, which are not to be considered limiting in any way.

EXAMPLE 1
Transfection of *M. smegmatis* spheroplasts with mycobacteriophage D29 DNA Spheroplasts of the *M. smegmatis* strain mc$^2$6 were prepared according to the following method. mc$^2$6 is a single colony isolate that is the predominant colony type isolated from the ATCC 607 *M. smegmatis* stock culture. It forms orange rough colonies on regeneration media. Hopwood, D. A. et. al., *In: Genetic Manipulation of the Streptomyces-A Laboratory Manual*, The John Innes Foundation, Norwich, England (1985).

Spheroplasts of *M. smegmatis* were prepared as for Streptomyces, using media for spheroplast preparation described by Udou et. al. for *M. smegmatis*. Udou, T. et al., *Journal of Bacteriology*, 151: 1035–1039 (1982). mc$^2$6 cells were grown in 40 ml of tryptic soy broth containing 1% glucose and 0.2% Tween 80 in a 250-ml baffled-flask at 37° C. with moderate shaking to an $A_{600}$-0.2, at which time a 20% glycine solution was added to a final concentration of 1%. The cells were incubated for an additional 16 hours and then harvested at room temperature by centrifuging at 5000×g for 10 minutes. The pellet was washed twice with 10 ml of 10.3% sucrose and then resuspended in protoplast (P) buffer containing 2 mg/ml lysozyme solution. After a 2-hour incubation at 37° C., 5 ml of P buffer was added and the spheroplasts were pelleted by centrifuging at 3000×g for 7 min. The pellet was resuspended in 10 ml P buffer and used within 3 hours.

mc$^2$-11 was isolated as a spontaneous D29-resistant isolate of the ATCC 607 *M. smegmatis* stock culture when $10^8$ cells were mixed with 3×$10^8$ D29 plaque-forming units and plated on tryptic soy agar plates. D29-resistant colonies arose at a frequency of $10^{-7}$.

mc$^2$6 spheroplasts were mixed with 1 ug of D29 DNA; one tenth of the resulting mixture was plated on tryptic soy agar plates, with or without 0.5M sucrose. They were then overlayed with the appropiate soft agar containing $10^8$ mc$^2$6 cells. The DNase treatment was performed by adding DNase I (Sigma), at a final concentration of 50 ug/ml, to the D29 DNA.

Equivalent amounts of mc$^2$11 spheroplasts were used in the same manner, but then subsequently overlayed with mc$^2$6 cells to assay plaque forming units (pfu).

Phage Plate Stocks: Plate lysates of D29 were prepared on tryptic soy agar media containing 2 mM $CaCl_2$. *M. smegmatis* cells that had been grown in a baffled flask at 37° C. in Middlebrook 7H9 broth containing ADC enrichment to midlog phase were mixed with phage diluted in MP buffer (10 mM Tris-HCl, pH 7.6 -10 mM $MgCl_2$-100 mM NaCl-2 mM $CaCl_2$) and incubated at 37° C. for 36 hours, until plates were confluent. The phage were harvested with MP buffer and then purified on two CsCl equilibrium gradients, followed by extensive dialysis against MP buffer. DNA was extracted from phage by adding EDTA to a final concentration of 50 mM and treating with proteinase K at 100 ug/ml at 55° C. for 24 hours, followed by phenol-chloroform extraction, and extensive dialysis against TE buffer.

Transfection: For each transfection, 2.5 ml of the spheroplast suspension was pelleted in a conical 15-ml polystyrene tube. The supernatant fluid was carefully decanted and the spheroplasts were resuspended in the remaining drop of buffer. After adding 1 ug of DNA in a total volume of less than 10 ul, 0.5 ml of a 25% PEG-1000 (J. T. Baker Chemical Co., Phila, Pa.) solution prepared in P buffer was added. The resulting combination was mixed. Within 3 min, 5 ml of P buffer was added to the mixture and the spheroplasts were pelleted as above. After carefully pouring off the supernatant fluid, the pellet was resuspended in 1 ml of P buffer and samples were transferred to tryptic soy agar with or without 0.5M sucrose. The plates were then overlayed with 3.0 ml of soft tryptic soy agar and incubated at 37° C. The plaques were counted after 24 hours of incubation.

EXAMPLE 2
Construction of the shuttle plasmid phAE1

TM4 phage DNA was ligated at a concentration of 250 ug/ml. Aliquots were partially digested with Sau3A that was serially diluted; fragments that averaged 30 to 50 kb in length (as analyzed by agarose gel electrophoresis gel electrophoresis) were obtained in this manner. These fragments were ligated at a 1:2 molar ratio of TM4 fragments to pHC79 that had been cleaved with BamHI. The packaging of an aliquot of this ligation with in vitro packaging mix (Gigapack plus, Stratagene, San Diego, Calif.) and subsequent transduction into ER1381 (hsdR mcrA$^+$ mcrB$^+$, E. Raleigh), yielded $10^6$ ampicillin colonies per ug of TM4 DNA insert, when plated on L agar containing ampicillin at 50 ug/ml.

A pool of 40,000 ampicillin-resistant clones was prepared by homogenizing colonies in L broth with a glass spreader. Plasmid was isolated from pools of clones by alkaline-SDS extraction, followed by phenol-chloroform extraction and concentration with ethanol. Covalently-closed plasmid DNA was transfected into mc$^2$6 spheroplasts as described in Example 1. The plaques were screened for the presence of pHC79 by performing plaque lifts using the protocol of Benton and Davis and Biotrans nylon membranes (ICN). Benton, W. D. and R. W. Davis, *Science*, 196: 180–182 (1977). The membranes were hybridized with pHC79 DNA that had been nick-translated with $^{32}$P-dCTP and autoradiography was performed.

EXAMPLE 3
Infection of BCG and *M. smegmatis* with shuttle plasmid phAE1

BCG-Glaxo (W. Jones) was propagated in Middlebrook 7H9 broth (Difco) containing ADC enrichment (Difco) and 0.5% Tween 80 (Sigma) in standing cultures at 37° C. Lawns of BCG-Glaxo or mc$^2$6 cells were prepared by mixing $10^8$ BCG-cells with supplemented top soft agar and pouring on Dubos agar without Tween 80 (Gibco) supplemented with OADS enrichment (Difco). Jones, W. D., Jr., *Tubercle,* 60: 55–58 (1979). The 4 phages, DS6A, TM4, phAE1, and 33D were serially diluted and spotted on the two lawns. The plates were read at 14 days and 2 days for BCG-Glaxo and *M. smegmatis,* respectively.

EXAMPLE 4

Cloning of aminoglycoside phoshotransferase gene into phAEI

A 1.6 kb EcoRI fragment encoding the aminoglycoside phosphotransferase gene (aph) from Tn903 was cloned into phAE1 by taking advantage of cosmid cloning strategy. Plasmid phAE1 DNA was isolated from *E. coli* and cut with EcoRI, the 1.6 kb fragment was ligated to these large DNA molecules. The ligation product was packaged into phage lambda in vitro, yielding particles which transduced kanamycin-resistance and ampicillin-resistance to *E. coli* cells. Plasmid DNA was isolated from these *E. coli* cells and shown to yield high frequencies of plaque-forming units when transfected into *M. smegmatis* mc$^2$6 protoplasts. This demonstrates that it is possible to clone at least 1.6 kb of additional DNA into the unique EcoRI site of phAE1. Similar results were obtained with the shuttle plasmid phAE2, a shuttle vector which has similar characteristics to those of phAE1 but is 2 kb smaller in size than phAE1, which should allow for the cloning of at least 3.6 kb of additional DNA. In both cases, introduction of the aph gene resulted in introduction of a new NruI site, providing proof that additional DNA fragments can be cloned and stably maintained in the shuttle phasmids. Thus, these vectors without further modification can be useful for cloning additional genes into mycobacteria.

EXAMPLE 5

Stable expression of a selectable marker in mycobacteria using a shuttle plasmid Shuttle phasmids were constructed from the phage L1 (ATCC #27199) in a manner similar to those constructed for the TM4 phage. Doke, S., *Kumamoto Medical Journal,* 34:1360–1373 (1960). All of the L1-shuttle phasmids identified have the ability to lysogenize *M. smegmatis.* L1 has been shown to integrate into *M. smegmatis* chromosomal material and to form stable lysogens. Other phage, such as L3 (ATCC #27200), a phage which remains as a plasmid (extrachromosomal) and L5 (ATCC #27201) can also be used in constructing shuttle phasmids. Results showed that these shuttle phasmids will lysogenize *M. smegmatis* and thus made it possible to stably integrate DNA of interest into mycobacteria for the first time. The aph gene was cloned into the unique EcoRI site of the L1-shuttle plasmid designated phAE15, as described above for the TM4-shuttle phasmids in *E. coli. M. smegmatis* cells (mc$^2$6) were overlayed on top of agar on a Dubos agar plate containing kanamycin. Dilutions of the shuttle plasmid phAE15 and phAE19 (phAE15 with the clone aph gene) were spotted on the agar lawn. The plate was incubated 5 days at 37° C. for 5 days. The colonies that grew all had been lysogenized with the L1-shuttle plasmid into which the aph gene had been cloned. The resulting shuttle plasmid, phAE19, was able to lysogenize *M. smegmatis* cells. The resulting lysogens expressed the cloned aph gene because they were resistant to kanamycin. Furthermore, these lysogens yielded mycobacteriophage particles that also expressed the kanamycin-resistant phenotype upon subsequent transfer and lysogenization of kanamycin-sensitive *M. smegmatis* cells. Transfer of these phages results in cotransduction of the lysogenic state (i.e. immunity to superinfection) and kanamycin resistance. The L1 phage, used to lysogenize *M. smegmatis,* does not plaque on BCG. However, variants of both L1 and the shuttle plasmid phAE19 which do form placques on BCG have been isolated. These can be tested for their ability to introduce and stably express genes of interest in BCG and *M. tuberculosis* by means of temperate shuttle phasmids. Thus, these phages have the ability to stably introduce DNA of interest into *M. smegmatis.* In addition, host range variants (e.g., phAE19) which will infect and lysogenize BCG have been isolated. This has made it possible to produce a recombinant mycobacterium, containing DNA of interest. Such recombinant mycobacteria can be used as a vaccine.

EXAMPLE 6

Integration of mycobacteriophage L1 and L1-shuttle plasmid DNA into the *M. smegmatis* chromosome Phage L1 was obtained by plating the culture supernate from an unspeciated Mycobacterium, ATCC 27199, grown in tryptic soy broth containing 0.05% Tween 80, on cloned *M. smegmatis* strain, mc$^2$6. Jacobs, W. R. Jr., Tuckman, M. & Bloom, B. R. *Nature,* 327:532–535 (1987). The phage was plaque-purified and high-titered plate lysates were obtained from mc$^2$6 grown on Dubos agar medium (without Tween) containing 2 mM CaCl$_2$ at 37° C. Phage particles were purified by CsCl equilibrium-density centrifugation and phage DNA was isolated as described previously. Jacobs, W. R. Jr., Tuckman, M & Bloom, B. R. *Nature,* 327:532–535 (1987). L1-shuttle phasmids were constructed following the previously described protocol using pHC79 as the cosmid and the substitution of L1 DNA for TM4 DNA. Jacobs, W. R. Jr., Tuckman, M. & Bloom, B. R. *Nature,* 327:532–535 (1987). The aph gene from Tn903 was introduced into one L1-shuttle plasmid, phAE154, by ligating phAE15 DNA cleaved at the unique EcoRI site to the Tn903 EcoRI aph cassette (Pharmacia). The resulting ligation was packaged in vivo into lambda-phage heads, which were then transduced into the *E. coli* strain 2338, selecting for both ampicillin- and kanamycin-resistance. Jacobs, W. R. et al. *Proc. Natl. Acad. Sci. U.S.A.,* 83: 1926–1930 (1986). Plasmid DNA was isolated from the *E. coli,* transfected into mc$^2$6 protoplasts and the resulting mycobacteriophage was designated phAE19. Lysogens were purified from turbid plaques arising after spotting phasmids on agar containing mc$^2$6 cells. Putative lysogens were tested for release of phages and resistance to superinfection by L1. Chromosomal DNA was isolated using a Braun homogenizer, followed by phenol-chloroform extractions. The Southern analysis was performed using Biotrans (ICN) nylon membranes following the manufacture's recommendations. L1 DNA was radiolabelled using a nick translation kit (BRL) and [$\chi$-$^{32}$P]-dCTP (Amersham).

EXAMPLE 7

Expression of kanamycin-resistance by lysogeny using the temperate shuttle plasmid phAE19

Figure 7:
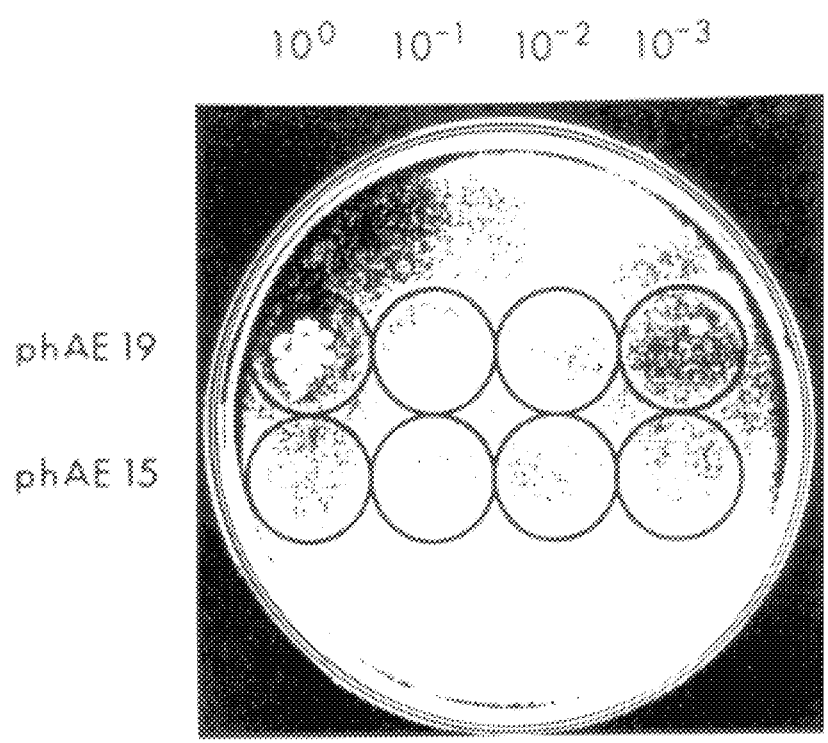
FIG. 7 shows expression of kanamycin-resistance by lysogeny using the temperate shuttle plasmid phAE19. Colonies appeared where phAE19 lysogenized mc²6 cells, thus demonstrating expression of kanamycin-resistance. In multiple experiments, kanamycin-resistance colonies were not observed from either spontaneous mutants of mc²6 cells or mc²6 cells lysogenized with phAE15.

*M. smegmatis,* mc$^2$6, [$2\times10^7$] cells, grown in shaking cultures at 37° C. in Middlebrook 7H9 broth supplemented with ADC enrichment and 0.05% Tween 80 (M-ADC-TW broth), were mixed with 3 ml Dubos top agar and overlayed onto a Dubos agar plate containing 15 ug/ml kanamycin. Lysates of the L1-shuttle phasmids, phAE15 and phAE19 (-phAE15::aph), were filtered through a 0.45 um filter and diluted to approximately $5\times10^6$ pfu/ml using MP buffer. Jacobs, W. R. Jr., Tuckman, M. & Bloom, B. R. *Nature,* 327: 532–535 (1987). Serial tenfold dilutions (10 ul) were spotted in the designated areas, and the plates were incubated for 5 days at 37° C. As shown in FIG. 7, colonies appeared where phAE19 lysogenized mc$^2$6 cells, thus demonstrating expression of kanamycin-resistance. In multiple experiments, kanamycin-resistance colonies were not observed from either spontaneous mutants of mc$^2$6 cells or mc$^2$6 cells lysogenized with phAE15. The *M. smegmatis* strain, designated mc$^2$96, which is mc$^2$6 lysogenized with phAE19 was deposited Jul. 22, 1988. at the American Type Culture Collection (Rockville, Md.) under Accession No. 67746. All restrictions on public access to the deposit will be removed irrevocably upon grant of a United States patent based on this application.

EXAMPLE 8
Construction and analysis of *E. coli*-mycobacteria shuttle plasmids

Plasmid pAL5000 DNA, isolated as described previously, was partially digested with MboI and linear fragments of 5 kb were isolated from an agarose gel following electrophoresis. Birnboim, H. & Doly, J. *Nucleic Acid Res.*, 7:1513–1525 (1979). These fragments were ligated to the positive selection vector pIJ666, which contain the neo gene originating from Tn5, and the P15A origin Of replication and cat gene from pACYC184, that had been cleaved with BamHI and EcoRV and transformed into *E. coli*. Kieser, T. and R. E. Melton, *Gene*, 65:83–91 (1988); Berg, D. E. et al., *Proc. Natl. Acad. Sci. U.S.A.*, 72:3628–3632 (1975); Chang, A. C. Y. and S. N. Cohen, *J. Bact.*, 134:1141–1156 (1978) and Chi, T. et al, *J. Bact.*, 133:816–821 (1978). Chloramphenicol-resistant transformants (200 colonies, resistant to 25 g/ml) were pooled and grown in mixed culture, from which plasmids were isolated. Birnboim, H. and J. Doly, *Nucleic Acid Res.*, 7:1513–1525 (1979). This library of pIJ666::pAL5000 hybrid plasmids was transformed into *M. smegmatis* by electroporation using the Gene Pulser (Biorad) electroporator. Chassy, B. M. and T. L. Flickinger *FEMS Microbiology Letters*, 44:173–177 (1987). Fresh cultures of mc$^2$6 cells were grown in M-ADC-TW broth with shaking to an A$_{600}$-1.7. The cells were harvested by centrifugation, washed in electroporation buffer (7 mM phosphage, pH7.2–272 mM sucrose) and resuspended to one tenth the original volume. Plasmid DNA (1 ug) was added to an electroporation cuvette containing 0.8 ml of *M. smegmatis* cells. Following a 10 minute incubation on ice, the cells were subjected to a single pulse of electroporation (25 uF at 6250 V/cm), then mixed with an equal volume of M-ADC-TW broth and incubated at 37° C. for 2 hours. The cells were then plated on 7H10 agar plates containing 10 ug/ml kanamycin and incubated for 7 days at 37° C. The kanamycin-resistant transformants were subcultured in 7H9-ADC-TW both containing 10 ug/ml kanamycin and retained their ability to plaque phage D29, confirming that they were *M. smegmatis*. Froman, S. et al., *Am. J. Public Health*, 44:1326–1334 (1954). These transformants were also resistant to 100 ug/ml of chloramphenicol. Plasmid DNA was isolated from 1 ml sample of cells by a modification of the procedure of Birnboim and Doly, incubating overnight sequentially in lysozyme, alkaline-SDS and finally high-salt. The DNA isolated from *M. smegmatis* was transformed into 2338 and yielded more than 10$^4$ kanamycin-resistant *E. coli* transformants per ug of DNA. Birnboim, H. and J. Doly, *Nucleic Acids Res.*, 7:1513–1525 (1979). All unique plasmids isolated from individual *E. coli* transformants could transform and confer kanamycin- and chloramphenicol-resistance to *M. smegmatis*.

EXAMPLE 9
Transformation of *M. smegmatis* and BCG with shuttle plasmid DNA

The BCG-Pasteur substrain P1173P2 was grown in M-ADC-TW broth shaking at 37° C. for 5 days (estimated viability 4.5×10$^7$ cfu/ml). These cells were transformed by electroporation with the pIJ666:pAL5000 recombinant library following the same procedure described above and plated on 7H10 agar containing ADC enrichment and 20 ug/ml of kanamycin. A pool of 45 kanamycin-resistant BCG cells was cultured in liquid medium containing 20 ug/ml of kanamycin for 3 weeks at 37° C. From this culture, plasmids were isolated as described in Example 8. They were all 11.2 kb in size and conferred kanamycin-resistance upon *E. coli* cells when transformed. This plasmid DNA was again used to transform BCG cells. The plates shown above were incubated for 18 days at 37° C. and then photographed. BCG-Pasteur substrain transformed with a shuttle plasmid, designated pYUP1100 (also referred to or designated pYUB13), which includes the gene encoding kanamycin resistance and the gene encoding chloramphenicol resistance, was deposited Jul. 22, 1988 at the American Type Culture Collection (Rockville, Md.) under Accession No. 67745. All restrictions on public access to the deposit will be removed irrevocably upon grant of a United States patent based on this application.

The *M. leprae* gene encoding stress-induced 65 kDa antigen has also been introduced and expressed in *M. smegmatis* and BCG. The *M. leprae* gene was cloned into an *E. coli*-Mycobacteria shuttle plasmid, designated pYUB12, which is a member of the group of shuttle plasmids, previously designated pYUP, which includes pYUP1100. The resulting construct, pYUB39, was transformed into both *M. smegmatis* and BCG-Pasteur and cell lysates from transformants were electrophoresed on SDS-polyacrylamide gels. The resulting gel was blotted onto nylon membrane that was then probed with a mouse monoclonal antibody that recognizes the *M. leprae*-specific epitope IIE9. The blot was then probed with mouse-specific rabbit antibodies linked to alkaline phosphatase, developed for phosphatase activity, and photographed. The resulting gel demonstrates that the cloned gene encoding the foreign *M. leprae* 65 kDa antigen is expressed in both *M. smegmatis* and BCG, as represented in FIG. 17, which is a photograph of the Western blot analysis of the SDS polyacrylamide gel electrophoresis of cell lysates containing the recombinant plasmids pYUB12 or pYUB39.

EXAMPLE 10
Construction of a recombinant plasmid for introduction of the Kan gene into *M. smegmatis* and integration of Kan into *M. smegmatis* genome The following bacterial strains were used: RY1103 (DB6507, Bach, M. L. et al., *Proceedings of the National Academy of Sciences, USA*, 76:386–390 (1979)) HB101, pyrF::Tn5,thr-,leu-,pro-,B1-,r-,m-,suII and RY1107 (DB6566, Rose, M. et al., *Gene*, 29:113–124 (1984)) B15, pyrF::Mu,trp$_{am}$,lacZ$_{am}$,hsdR$^-$,m$^+$,Su$^{31}$. Both were obtained from Dr. David Botstein (Massachusetts Institute of Technology). Y1109(DH5alpha)F$^-$,endA1,hsdR17(rK,mK$^+$), supE44, thi1, recA1, gyrA96, rela, del (argF-lacZYA) U169, lambda$^-$,phi80dlacZde1M15, which was obtained from Bethesda Research Laboratories. MC$^2$-6, a single colony isolate *M. smegmatis* prototroph, which was obtained from Dr. William Jacobs (Albert Einstein College of Medicine). FOA$^R$-3 is a spontaneous mutant of MC$^2$-6 to uracil auxotrophy and resistance to 5-fluoro-orotic acid. *M. bovis*-BCG (Moreau) is ATCC 35736. *M. bovis*-BCG (Montreal) is ATCC 35735.

Mycobacterial Genomic DNA Libraries

*M. smegmatis* genomic DNA was obtained from MC$^2$-6 after growth in tryptic soy broth supplemented with glucose and Tween 80. Cultures were grown to saturation with glycine added to 0.5% for the last several hours. Cells were harvested by centrifugation, washed and resuspended in 50 mM Tris pH8.0, 10 mM EDTA, 10% sucrose and then treated with 0.2 mg. per ml. lysozyme for one hour, followed by 50 mM EDTA and 1% SDS for 15 minutes. Multiple phenol:chloroform extractions were performed, followed by isopropanol precipitation, RNAse treatment, phenol:chloroform extraction, chloroform extraction and ethanol precipitation. The pellets were washed with 70% ethanol and resuspended in TE pH7.5. *M. bovis*-BCG (Moreau) genomic DNA was a generous gift of Dr. Graskinsky.

Mycobacterial genomic DNA was partially digested with Sau3A, size selected by agarose gel electrophoresis onto DE81 paper, eluted with high salt, ethanol precipitated and ligated into pUC19 which had been cleaved with BamHI and treated with calf intestinal phosphatase. DH5alpha, made competent for transformation by the procedure of Hanahan, were transformed with this ligation and plated onto Luria Bertani agar containing 50 ug/ml ampicillin. The proportion of colonies containing recombinant plasmids was determined by plating onto indicator plates containing XGa1 and IPTG and determining the ratio of white colonies to total (white plus blue) colonies. Pooled plasmid DNA was obtained by scraping colonies from the plates, resuspending in 50 mM Tris pH 8.0, 10 mM EDTA, 50 mM glucose. The resulting suspension was processed by the alkaline lysis method for obtaining plasmid DNA. The *M. smegmatis* recombinant DNA library consists of 35,000 independent initial transformants, of which 85% were recombinant. The *M. bovis*-BCG recombinant DNA library consists of 64,000 independent initial transformants of which 55% were recombinant.

Isolation of recombinant plasmids containing the mycrobacterial pyrF gene

Y1103 and Y1107 were made competent by the method of Hanahan, transformed with the plasmid library DNA and plated on minimal agar plates. Of 180,000 transformants initially screened for the *M. smegmatis* library, 31 were able to grow on minimal medium.

Plasmid DNA Isolation, Restriction Mapping and DNA Sequencing

Plasmid DNA was isolated from liquid cultures by the alkaline lysis method. Restriction mapping of recombinant plasmid DNA was performed with multiple enzymes using standard methods. DNA sequencing was performed using the dideoxy method after subcloning into M13mp18 and M13mp19, using sequencing kits from New England Biolabs and U.S. Biochemicals.

EXAMPLE 11

Integration of the *M. leprae* 65 KD gene into *M. smegmatis* genomic DNA

Construction of recombinant plasmids expressing kanamycin resistance and the *M. leprae* 65 kD antigen pPP25, a recombinant plasmid containing DNA from *M. smegmatis* able to complement pyrF⁻ *E. coli*, was digested with BamHI and ligated to the 1.3 kB BamHI fragment encoding aminoglycoside phosphotransferase of Tn903, isolated from pUC4kSAC. The Eco RI fragment of Y3178 containing the gene encoding the *M. leprae* 65 kD antigen was subsequently cloned into the unique XhoI and EcoRV sites in the mycobacterial DNA in this plasmid. In each case the transcriptional orientations of the mycobacterial open reading frame, the kanamycin resistance gene and the *M. leprae* 65 kD gene were determined to be in the same orientation.

Transformation of Mycobacteria by Electroporation

*M. smegmatis* and *M. bovis*-BCG were grown in Middlebrook 7H9 medium supplemented with ADC enrichment and 0.05% Tween 80 (M-ADC-Tw) to an $A_{600}$ of approximately 0.3 to 0.5. Cells were harvested by centrifugation, washed in 10 mM Hepes pH7.0, centrifuged and resuspended in 1/10 volume 10 mM Hepes pH7.0, 10% glycerol (*M. smegmatis*), or washed and resuspended in 1/10 volume 7 mM sodium phosphate pH 7.2, 272 mM sucrose (BCG). DNA was added and the cells were exposed to a single pulse of 6.25 kV/cm at 25 microfarads using the Biorad Gene Pulser. Three to five volumes of M-ADC-Tw were then added, the cells were incubated for 2–3 hours at 37° C., centrifuged, resuspended in a small volume of M-ADC-Tw and plated on tryptic soy agar supplemented with 1% glucose, containing 10 ug/ml kanamycin (*M. smegmatis*) or Middlebrook 7H10 agar supplemented with ADC enrichment containing 10 ug/ml kanamycin.

Southern Blot Analysis

Genomic DNA from mycobacterial transformants was digested with restriction enzymes, electrophoresed in agarose gels, transferred to nitrocellulose and probed with DNA labelled with $^{32}P$ by nick translation, all using standard procedures.

Western Blot (Immunoblot) Analysis

Expression of the 65 kD *M. leprae* protein was demonstrated using Western blot techniques. Lysates of mycobacterial and *E. coli* transformants were subjected to SDS polyacrylamide gel electrophoresis, electro-transferred to nitrocellulose, and probed with the monoclonal antibody IIIE9 at a dilution of approximately 1:1000 using standard techniques. The Protoblot kit (Promega Biotec) was used to detect binding of the antibody and was used according to the manufacturer's instructions. This resulted in detection of expression of the 65 kD protein in cells transformed with the plasmid containing the *M. leprae* gene.

Equivalents

Those skilled in the art will recognize, or be able to ascertain, using no more than routine experimentation, many equivalents to the specific embodiments of the invention described specifically herein. Such equivalents are intended to be encompassed in the scope of the following claims.

We claim:

1. A recombinant mycobacterium capable of expressing DNA encoding a selectable marker incorporated therein, wherein the DNA encoding the selectable marker is stably integrated into genomic DNA of the recombinant mycobacterium.

2. The recombinant mycobacterium of claim 1, which is selected from the group consisting of:

a. *Mycobacterium smegatis;* b. *Mycobacterium bovis*-BCG;

c. *Mycobacterium avium;* d. *Mycobacterium phlei;* e. *Mycobacterium fortuitum;* f. *Mycobacterium lufu;* g. *Mycobacterium tuberculosis;* h. *Mycobacterium habana;* i. *Mycobacterium scrofulaceum;* j. *Mycobacterium intracellare*; and k. any genetic variants thereof.

3. The mycobacterium of claim 1, wherein the DNA encoding the selectable marker is a gene encoding antibiotic resistance.

4. The mycobacterium of claim 3, wherein the antibiotic is selected from the group consisting of kanamycin, viomycin, thiostrepton, hygromycin and bleomycin.

5. The mycobacterium of claim 4, wherein the antibiotic is kanamycin.

6. A recombinant *Mycobacterium tuberculosis* capable of expressing DNA encoding a selectable marker incorporated therein, wherein the DNA encoding the selectable marker is stably integrated into genomic DNA of the recombinant *Mycobacterium tuberculosis*.

7. The mycobacterium of claim 6, wherein the DNA encoding the selectable marker is a gene encoding antibiotic resistance.

8. The mycobacterium of claim 7, wherein the antibiotic is selected from the group consisting of kanamycin, viomycin, thiostrepton, hygromycin and bleomycin.

9. The mycobacterium of claim 8, wherein the antibiotic is kanamycin.

10. A recombinant *Mycobacterium bovis*-BCG capable of expressing DNA encoding a selectable marker incorporated therein, wherein the DNA encoding the selectable marker is stably integrated into genomic DNA of the recombinant *Mycobacterium bovis*-BCG.

11. The mycobacterium of claim 10, wherein the DNA encoding the selectable marker is a gene encoding antibiotic resistance.

12. The mycobacterium of claim 11, wherein the antibiotic is selected from the group consisting of kanamycin, viomycin, thiostrepton, hygromycin and bleomycin.

13. The mycobacterium of claim 12, wherein the antibiotic is kanamycin.

14. The mycobacterium of claim 1, wherein an endogenous mycobacterial gene is replaced by the DNA encoding the selectable marker.

15. The mycobacterium of claim 1, wherein an endogenous mycobacterial gene is rendered nonfunctional by the DNA encoding the selectable marker.

16. The mycobacterium of claim 6, wherein an endogenous mycobacterial gene is replaced by the DNA encoding the selectable marker.

17. The mycobacterium of claim 6, wherein an endogenous mycobacterial gene is rendered nonfunctional by the DNA encoding the selectable marker.

18. The mycobacterium of claim 10, wherein an endogenous mycobacterial gene is replaced by the DNA encoding the selectable marker.

19. The mycobacterium of claim 10, wherein an endogenous mycobacterial gene is rendered nonfunctional by the DNA encoding the selectable marker.

* * * * *